United States Patent
Iwashita et al.

(10) Patent No.: US 11,236,060 B2
(45) Date of Patent: Feb. 1, 2022

(54) METHOD FOR PRODUCING SOLID DISPERSION CONTAINING NOBILETIN

(71) Applicant: KAO CORPORATION, Tokyo (JP)

(72) Inventors: Masazumi Iwashita, Saitama (JP); Takashi Suzuki, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 17/040,245

(22) PCT Filed: Mar. 20, 2019

(86) PCT No.: PCT/JP2019/011789
§ 371 (c)(1),
(2) Date: Sep. 22, 2020

(87) PCT Pub. No.: WO2019/182032
PCT Pub. Date: Sep. 26, 2019

(65) Prior Publication Data
US 2021/0017144 A1    Jan. 21, 2021

(30) Foreign Application Priority Data

Mar. 22, 2018 (JP) .............................. JP2018-054058

(51) Int. Cl.
*C07D 311/60* (2006.01)
(52) U.S. Cl.
CPC .................. *C07D 311/60* (2013.01)
(58) Field of Classification Search
CPC .................................................. C07D 311/60
See application file for complete search history.

(56) References Cited

U.S. PATENT DOCUMENTS

| | | | |
|---|---|---|---|
| 2002/0040052 A1 | 4/2002 | Ito et al. | |
| 2017/0273999 A1* | 9/2017 | Umehara | .................. A61Q 7/00 |
| 2019/0183852 A1* | 6/2019 | Iwashita | .................. A61P 43/00 |

FOREIGN PATENT DOCUMENTS

| | | | |
|---|---|---|---|
| CN | 104884054 A | | 9/2015 |
| EP | 1 829 542 A1 | | 9/2007 |
| EP | 2 292 214 B1 | | 7/2014 |
| JP | 11-169148 A | | 6/1999 |
| JP | 2002-60340 A | | 2/2002 |
| JP | 2014-001364 | * | 1/2014 |
| JP | 2014-1364 A | | 1/2014 |
| JP | 2018-131432 A | | 8/2018 |
| WO | WO 2006/049234 A1 | | 5/2006 |
| WO | WO 2018/025871 A1 | | 2/2018 |

OTHER PUBLICATIONS

International Search Report dated Jun. 11, 2019 in PCT/JP2019/011789 filed on Mar. 20, 2019, 1 page.
"Does Alzheimer's disease improve in the peel of a mandarin orange? Clinical effects of the NChinpi on the cognitive impairment of patients Alzheimer's disease", Journal of Pharmacological Sciences, 2015, vol. 145, pp. 234-236 (8 total pages) (with unedited computer-generated English translation).

* cited by examiner

*Primary Examiner* — Valerie Rodriguez-Garcia
(74) *Attorney, Agent, or Firm* — Oblon, McClelland, Maier & Neustadt, L.L.P.

(57) ABSTRACT

Provided are a nobiletin composition having excellent solubility in water and a method for simply producing the same. A method for producing a solid dispersion containing nobiletin, the method involving a step of dissolving nobiletin or a nobiletin-containing substance and a water-soluble hesperidin derivative selected from the group consisting of glucosyl hesperidin and methyl hesperidin in an ethanol aqueous solution having an ethanol concentration of from 20 to 90 vol % and a step of drying the solution.

3 Claims, 14 Drawing Sheets

METHOD FOR PRODUCING SOLID DISPERSION CONTAINING NOBILETIN

CROSS REFERENCE TO RELATED APPLICATION

This application is a national stage entry under 35 USC 371 of PCT/JP2019/011789, filed on Mar. 20, 2019, and claims priority to Japanese Patent Application No. 2018-054058 filed on Mar. 22, 2018.

FIELD OF THE INVENTION

The present invention relates to a method for producing a solid dispersion comprising nobiletin.

BACKGROUND OF THE INVENTION

Nobiletin is one of polymethoxyflavonoids contained in citrus fruits such as Citrus unshiu and Shikuwasa. Nobiletin is known to have various physiological activities such as PPAR activating action and adiponectin secretion promoting action (Patent Literature 1), neurite outgrowth promoting action (Patent Literature 2) and memory disorder suppressing action (Non Patent Literature 1) and hence acknowledged as an important component of health foods.

However, nobiletin is poorly water-soluble and it is difficult to effectively use physiological functions of the active pharmaceutical ingredient itself for foods and drinks and pharmaceutical products.

Thus, techniques for solubilizing nobiletin in water have been studied and, for example, a method for preparing a cyclodextrin inclusion complex is reported (Patent Literature 3). However, this production method is known to have a difficulty in obtaining significant enhancement in an amount of solubilization.

On the other hand, it is reported that, in a polyphenol composition obtained by dissolving poorly water-soluble polyphenols and methylated poorly water-soluble polyphenols in an ethanol aqueous solution having a specific concentration and then drying, the solubility of the poorly water-soluble polyphenols in water is increased (Patent Literature 4). Particularly, when an amorphous solid dispersion can be obtained by using the present production method, the supersaturated dissolution of poorly water-soluble polyphenol expectedly causes a notable solubility increase exceeding the method of cyclodextrin inclusion complex and the like. However, the literature does not describe the solubilization of nobiletin at all and the effect thereof is uncertain.

(Patent Literature 1) International Publication No. WO2006/049234

(Patent Literature 2) JP-A-2002-60340

(Patent Literature 3) JP-A-11-169148

(Patent Literature 4) JP-A-2014-1364

(Non Patent Literature 1) Journal of Pharmacological Sciences, 2015, 145, 234-236

SUMMARY OF THE INVENTION

The present invention relates to the following (1) to (3).
(1) A method for producing a solid dispersion comprising nobiletin, the method comprising a step of dissolving nobiletin or a nobiletin-containing substance and a water-soluble hesperidin derivative selected from the group consisting of glucosyl hesperidin and methyl hesperidin in an ethanol aqueous solution having an ethanol concentration of from 20 to 90 vol % and a step of drying the solution.
(2) A nobiletin-containing solid dispersion obtained by the production method of (1) and having a degree of crystallinity of nobiletin of 10% or less as calculated from an X-ray diffraction spectrum.
(3) A pharmaceutical product, a quasi-pharmaceutical product, or a cosmetic product comprising the nobiletin-containing solid dispersion of (2).
(4) A food or a drink comprising the nobiletin-containing solid dispersion of (2).

DETAILED DESCRIPTION OF THE INVENTION

Figure 1:
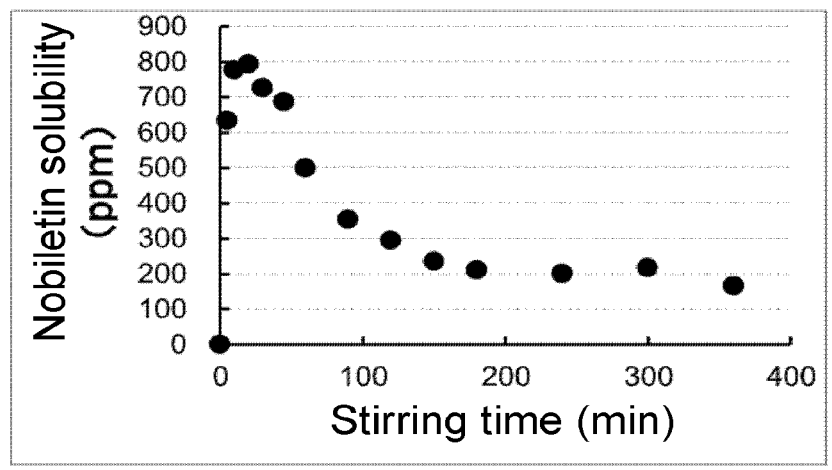
FIG. 1 shows dissolved concentration of nobiletin in the nobiletin-methyl hesperidin solid dispersion of Example 1.

The present invention relates to provision of a method for simply producing a nobiletin composition having excellent solubility in water.

The present inventors extensively studied in view of the above problem and found that when nobiletin or a nobiletin-containing substance is dissolved in an ethanol aqueous solution and the obtained solution is dried, a solid dispersion in which nobiletin is dispersed in the amorphous state can be obtained, and such a solid dispersion has extremely high solubility of nobiletin in water, retains the high solubility in water stably and has high biomembrane permeability.

According to the present invention, a nobiletin-containing solid dispersion having a notably enhanced the solubility of nobiletin in water can be provided. When the solid dispersion of the present invention is used, the enhancement in biomembrane permeability of nobiletin and the increase in physiological functions of nobiletin are expected. Additionally, the solid dispersion of the present invention does not use an organic solvent in the production process and hence is favorably used for foods and drinks.

The "nobiletin" in the present invention refers to 3',4',5,6,7,8-hexamethoxyflavone and has the following structure.

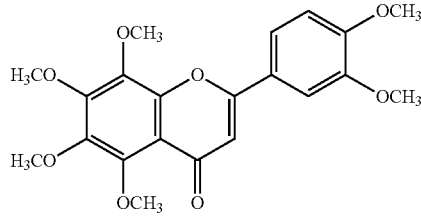 [SMILES: COc1ccc(-c2cc(=O)c3c(OC)c(OC)c(OC)c(OC)c3o2)cc1OC]

Nobiletin may be, for example, any of a chemically synthesized compound, a compound separated from a naturally occurring compound, a compound purified after separated from a chemically synthesized compound or a naturally occurring compound, and a commercial product.

The purity of nobiletin is not particularly limited and, for example, may be purity to the extent that a desired pharmacological effect is exerted when formed as a solid dispersion. For example, a "nobiletin-containing substance" which contains nobiletin in a high content ratio or a high content obtained by extracting citrus fruits and juice residues with an organic solvent in which nobiletin is soluble, such as methanol and ethanol, and suitably separating and purifying it can also be used. Examples of the nobiletin-containing substance include a Shikuwasa extract having a high nobiletin content (for example, "PMF90" <manufactured by Okinawa Research Center, nobiletin content ratio of about 60 mass %>).

Examples of the "water-soluble hesperidin derivative" used in the present invention include hesperidins with increased water-solubility by enzymatically or chemically treating hesperidin, and examples thereof include glucosyl hesperidin and methyl hesperidin in which a different sugar is bound to the sugar moiety (or rutinose moiety) of hesperidin such as glycosyl hesperidin and the like. Of these, from a viewpoint of water-solubility, methyl hesperidin and glucosyl hesperidin are preferable.

The "methyl hesperidin" is a mixture of several kinds of methylated products produced by methylating hesperidin (a compound of the following formula (2) wherein R is a hydrogen atom) using a methylating agent such as dimethyl sulfate and known to include mainly chalcone-type compounds (1) and flavanone type compounds (2), and examples of the structural component thereof include compounds having the following structure (for example, see Japanese Journal of Food Chemistry and Safety, 12 (2), 2005, 71-75).

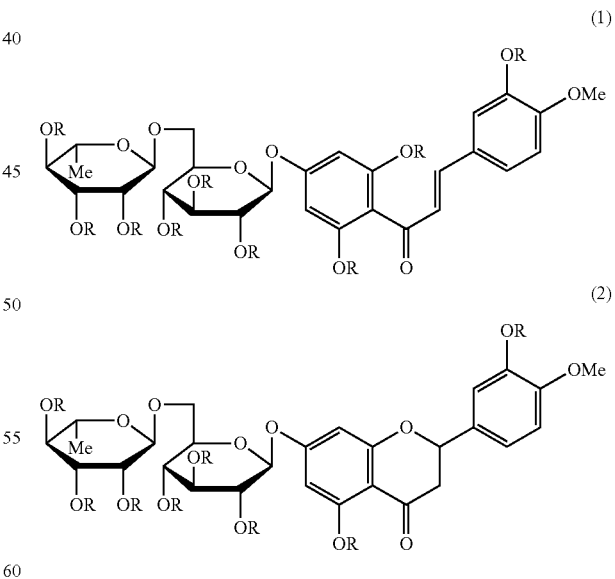

wherein R represents a hydrogen atom or a methyl group.

The "methyl hesperidin" in Japan is employed as a pharmaceutical additive name, a food additive name, and a cosmetic product ingredient name, and methyl hesperidin as a pharmaceutical additive and a food additive is mainly treated as a mixture of Compounds (3) and (4).

(3)

Rh—Gl—O—[ring with OMe, OR, C=O connected to CH=CH—phenyl(OMe)(OMe)]

|       | R  | Gl-2 | Rh-2 |
|-------|----|------|------|
| (3-1) | Me | Me₂  | H    |
| (3-2) | H  | Me   | H    |
| (3-3) | H  | H    | H    |

(4)

Rh—Gl—O—[flavanone ring with OR, O, C=O, phenyl(OMe)(OMe)]

|       | R | Gl-2 | Rh-2 |
|-------|---|------|------|
| (4-1) | H | Me   | Me   |
| (4-2) | H | Me   | H    |
| (4-3) | H | H    | H    | wherein Gl represents a glucose residue and Rh represents a rhamnose residue. Additionally, Gl-2 represents a group at the second position of the glucose residue (the case of (3-1) further includes a group at the third position) and Rh-2 represents a group at the second position of the rhamnose residue.)

Additionally, hesperidin methylchalcone as a cosmetic product ingredient is treated as a compound represented by (5). Compositions containing a large amount of the chalcone-type compounds are also called hesperidin methylchalcone.

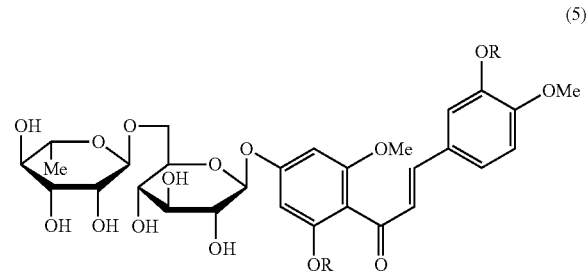

(5)

wherein R is a hydrogen atom or a methyl group.

Methyl hesperidin used in the present invention may be one containing both chalcone-type compound (1) and flavanone-type compound (2) described above or may be one containing either one of them.

More preferable methyl hesperidin in the present invention include mixtures of Compounds (3) and (4).

Methyl hesperidin can be produced by a known method such as dissolving hesperidin in a sodium hydroxide aqueous solution, allowing an equivalent amount of dimethyl sulfate to act on the alkaline solution, neutralizing the reaction solution with sulfuric acid, extracting it with n-butyl alcohol, and after distilling off the solvent, recrystallizing with isopropyl alcohol (Sakieki, The Chemical Society of Japan Journal, 79, 733-(1958)), but the production method therefor is not limited thereto.

A commercial methyl hesperidin-containing formulation may be used as the methyl hesperidin and examples include "Methyl hesperidin" (Tokyo Chemical Industry, Co., Ltd.), "Hesperidin methylchalcone" (Sigma), "Methyl hesperidin" (Hamari Chemicals, Ltd.), "Methyl hesperidin" (SHOWA DENKO K.K.), and "Methyl hesperidin" (Alps Pharmaceutical Ind. Co., Ltd.).

Additionally, examples of glucosyl hesperidin include monoglucosyl hesperidin "αG hesperidin PA-T" (Toyo Sugar Refining Co., Ltd.), and "Hayashibara hesperidin (registered trademark) S" (Hayashibara Co., Ltd.).

The solid dispersion containing nobiletin of the present invention comprises a step of dissolving nobiletin or a nobiletin-containing substance and the water-soluble hesperidin derivative in an ethanol aqueous solution having an ethanol concentration of from 20 to 90 vol % at 25° C. and a step of drying the solution.

An ethanol concentration of the ethanol aqueous solution used for dissolving nobiletin or the nobiletin-containing substance and the water-soluble hesperidin derivative is preferably 25 vol % or more from a viewpoint of the solubility of nobiletin or the nobiletin-containing substance, and preferably 88 vol % or less from a viewpoint of the solubility of the water-soluble hesperidin derivative. Specifically, an ethanol concentration is more preferably 30 vol % or more, further preferably 35 vol % or more, further preferably 40 vol % or more, further preferably 50 vol % or more, further preferably 60 vol % or more, and further preferably 70 vol % or more, and more preferably 85 vol % or less, and further preferably 82 vol % or less. Additionally, an ethanol concentration is more preferably from 30 to 85 vol %, further preferably from 35 to 85 vol %, further preferably from 40 to 82 vol % or less, and further preferably from 45 to 82 vol %.

A dissolution method of nobiletin or the nobiletin-containing substance and the water-soluble hesperidin derivative in an ethanol aqueous solution is not particularly limited and, for example, can be carried out by mixing nobiletin or the nobiletin-containing substance and the water-soluble hesperidin derivative in any ratio and mixing the mixture with an ethanol aqueous solution.

When nobiletin or the nobiletin-containing substance and the water-soluble hesperidin derivative are mixed, a content of nobiletin in the mixture is, from a viewpoint of increasing a content of nobiletin in the solid dispersion, 1 mass % or more, more preferably 3 mass % or more, further preferably 4 mass % or more, further preferably 5 mass % or more, further preferably 7.5 mass % or more, further preferably 10 mass % or more, and further preferably 15 mass % or more, and is, from a viewpoint of easy processability, 90 mass % or less, more preferably 70 mass % or less, further preferably 60 mass % or less, further preferably 50 mass % or less, further preferably 45 mass % or less, further preferably 40 mass % or less, and further preferably 35 mass % or less. Additionally, a content of nobiletin in the mixture is from 1 to 90 mass %, more preferably from 3 to 70 mass %, further preferably from 4 to 60 mass %, further preferably from 5 to 50 mass %, further preferably from 7.5 to 45 mass %, further preferably from 10 to 40 mass %, further preferably preferably from 15 to 35 mass %, and particularly preferably 25 mass %.

A content of the water-soluble hesperidin derivative varies depending on the kind but in the mixture is, from a viewpoint of the solubility of nobiletin in water, 10 mass % or more, more preferably 20 mass % or more, further preferably 25 mass % or more, further preferably 30 mass % or more, further preferably 45 mass % or more, further preferably 60 mass % or more, and further preferably 65 mass % or more, and, from a viewpoint of easily preparing the solid dispersion, 99 mass % or less, more preferably 97 mass % or less, further preferably 96 mass % or less, further preferably 92.5 mass % or less, further preferably 90 mass % or less, and further preferably 85 mass % or less. Additionally, a content of methyl hesperidin in the mixture is from 10 to 99 mass %, more preferably from 20 to 97 mass %, further preferably from 25 to 96 mass %, further preferably from 30 to 92.5 mass %, further preferably from 45 to 90 mass %, further preferably from 60 to 85 mass %, further preferably from 65 to 85 mass %, and particularly preferably 75 mass %.

When nobiletin or the nobiletin-containing substance and the water-soluble hesperidin derivative are mixed in the present invention, a mass ratio of nobiletin to the water-soluble hesperidin derivative [nobiletin/water-soluble hesperidin derivative] is, from a viewpoint of increasing a content of nobiletin in the solid dispersion to be obtained and easily preparing the solid dispersion, preferably 0.01 or more, more preferably 0.03 or more, further preferably 0.04 or more, further preferably 0.07 or more, and further preferably 0.1 or more. Additionally, it is, from a viewpoint of increasing the solubility of nobiletin to be obtained in water, preferably 9 or less, more preferably 4 or less, further preferably 3 or less, further preferably 1 or less, and further preferably 0.67 or less. Additionally, it is preferably from 0.01 to 9, more preferably from 0.03 to 4, more preferably from 0.04 to 3, further preferably from 0.07 to 1, further preferably from 0.1 to 0.67, and particularly preferably 0.33.

A temperature of from 0° C. to 90° C. is sufficient for dissolving nobiletin or the nobiletin-containing substance and the water-soluble hesperidin derivative in the ethanol aqueous solution, and is preferable in that dissolution under such a temperature condition allows treatment at normal pressure and hence requires no special apparatus. The lower limit of dissolution temperature is, from a viewpoint of increasing the solubility of nobiletin or the nobiletin-containing substance, preferably 5° C. or more, and further preferably 10° C. or more. Additionally, the upper limit of dissolution temperature is, from a viewpoint of the energy efficiency and the boiling point of the ethanol aqueous solution, preferably 85° C. or less, more preferably 80° C. or less, further preferably 75° C. or less, further preferably 70° C. or less, and further preferably 60° C. or less. Specifically, a dissolution temperature is preferably from 5 to 85° C., more preferably from 10 to 80° C., further preferably from 10 to 75° C., further preferably from 10 to 70° C., and further preferably from 10 to 60° C.

After dissolution, a step of cooling the solution to preferably 50° C. or less, and further preferably 30° C. or less may be carried out as needed. Further, a step of removing the solid part from the solution may be carried out as needed. A method for removing the solid part is not particularly limited and, for example, centrifugation, decantation, or filtration can be carried out.

Subsequently, the obtained solution is subjected to a drying step.

The drying herein refers to the removal of the solvent from the solution. Examples of the drying unit include spray drying, evaporation to dryness, and freeze-drying. Of these, spray drying is preferable from a viewpoint of causing nobiletin or the nobiletin-containing substance to be in the non-crystalline solid state, further increasing the solubility of nobiletin or the nobiletin-containing substance in water, and enhancing the initial solubility of nobiletin or the nobiletin-containing substance.

A method of freeze-drying or spray drying is not particularly limited and a known method is applicable.

For example, in the case of spray drying, a spray dryer is preferably used.

Conditions for spray drying can be suitably determined and, for example, an inlet gas temperature is from 95 to 145° C., preferably from 100 to 140° C., and more preferably from 105 to 135° C., and an outlet gas temperature is from 50 to 90° C., preferably from 55 to 85° C., and more preferably from 60 to 80° C.

Additionally, it is preferable to determine the ranges of a spray solution supply speed being from 150 to 600 mL/h, a spray nitrogen flow rate being from 200 to 650 L/h, and an aspirator flow rate being from 25 to 35 $m^3/h$.

Additionally, in the case of freeze-drying, the treated solution is frozen in liquid nitrogen, a cool bath, or a freezer, crushed, separated by sieving and then the moisture is sublimated in a vacuum to dry. A freezing temperature of the treated solution is preferably from −70 to 0° C. An absolute pressure during drying is preferably from 0.1 to 1,000 Pa, more preferably from 0.5 to 100 Pa, and further preferably from 1 to 10 Pa.

Classification, granulation, and crushing and the like may be carried out as needed after spray drying or freeze-drying.

Such a treatment causes nobiletin to be amorphous and provides the solid dispersion containing nobiletin in the state of amorphous.

"Amorphous" means the state lacking a certain regularity in the molecular sequence. Amorphousness can be confirmed by powder X-ray diffraction.

In the present invention, nobiletin in the solid dispersion has preferably a degree of crystallinity of 50% or less, further preferably a degree of crystallinity of 40% or less, further preferably a degree of crystallinity of 20% or less, further preferably a degree of crystallinity of 10% or less, further preferably a degree of crystallinity of 5% or less, and particularly preferably a degree of crystallinity of 0%, which means complete amorphousness.

It is preferable that the solid dispersion of the present invention has no crystalline diffraction peak detected in powder X-ray diffraction measurement.

A degree of crystallinity of nobiletin can be calculated by the following method. First, peaks are separated into a crystalline diffraction line and an amorphous halo based on the diffraction intensity value by the X-ray diffractometry using the profile fitting technique without considering the impacts such as incoherent scattering and lattice distortion. Next, a degree of crystallinity of nobiletin is calculated from the integrated intensity of all peaks by the following formula [1].

$$\text{Degree of crystallinity of nobiletin (\%)} = [\Sigma I\alpha/(\Sigma I\alpha + \Sigma Iam)] \times 100 \quad [1]$$

[$\Sigma I\alpha$ is the sum of integrated intensity of all peaks of the crystalline diffraction line, and $\Sigma Iam$ is the sum of integrated intensity of all peaks of the diffraction line of amorphous part]

The thus obtained solid dispersion containing nobiletin (nobiletin-containing solid dispersion") of the present invention has quite excellent solubility in water (initial solubility and time-course solubility).

For example, as shown in Examples to be described later, time-course solubility of nobiletin (for example, in the case of adding the nobiletin-containing solid dispersion in water and stirring it for 6 hours, a nobiletin dissolved concentration (area under the curve from the start of stirring up to 6 hours later (horizontal axis: stirring time (unit=min), vertical axis: nobiletin solubility (unit=ppm)) is as extremely high as about $1.13 \times 10^5$ ppm·min and the high solubility is retained for a long time (FIG. 1 and Table 1-1). Such a high solubility is an unpredictable effect unobtainable in the solid dispersion produced by mixing a compound known as poorly water-soluble polyphenol (for example, ellagic acid) as is nobiletin with methyl hesperidin or αG hesperidin RA-T.

Additionally, the nobiletin-containing solid dispersion of the present invention has quite excellent permeability of nobiletin through the cell membrane derived from human small intestinal epithelial cell, which is also an unpredictable effect in the solid dispersion of the above other poorly water-soluble polyphenols. These effects are presumably achieved due to the obtention of the amorphous solid dispersion and due to the achievement of the supersaturated dissolution of nobiletin by the present production method.

Additionally, a water content in the solid dispersion is, from a viewpoint of easy refinement and good handleability, 20 mass % or less, further preferably 10 mass % or less, further preferably 7 mass % or less, and further preferably 5 mass % or less.

The solid dispersion containing nobiletin obtained by the production method of the present invention can be used for various foods and drinks, pharmaceutical products, quasi-pharmaceutical products, and cosmetic products. Above all, it is useful to utilize it for products dissolved in an aqueous solvent when used.

Examples of the food and drink include solid or semi-solid foods and drinks, e.g. instant drinks, breads, noodles, sweets such as cookies, snacks, jellies, dairy products, frozen products, instant foods such as powder coffee, starch processed products, processed meat products, other processed foods, seasoning, and dietary supplements. Preferable examples include solid instant foods and drinks eaten upon being dissolved in water or heated water when used. Additionally, examples of the pharmaceutical product or quasi-pharmaceutical product include dosage forms such as tablets (chewable, and the like), capsules, and powders. Additionally, examples of the cosmetic product preferably include cleansing agents such as soaps and whitening cosmetic agents.

An amount of the solid dispersion containing nobiletin added to the above foods and drinks, pharmaceutical products, quasi-pharmaceutical products, or cosmetic products is, from a viewpoint of the function expression and product size, 0.01 mass % or more, preferably 0.05 mass % or more, further preferably 0.1 mass % or more, further preferably 0.5 mass % or more, and further preferably 1.0 mass % or more. On the other hand, it is, from a viewpoint of taste, 90 mass % or less, preferably 80 mass % or less, further preferably 70 mass % or less, further preferably 60 mass % or less, and further preferably 50 mass % or less. Additionally, it is from 0.01 to 90 mass %, preferably from 0.05 to 80 mass %, further preferably from 0.1 to 70 mass %, further preferably from 0.5 to 60 mass %, and further preferably from 1.0 to 50 mass %.

The state of presence of the solid dispersion containing nobiletin in these formulations may be in a dissolved state or a dispersed state, but the state of presence thereof is irrelevant.

Aspects and preferable embodiments of the present invention are described below.

<1> A method for producing a solid dispersion comprising nobiletin, the method comprising a step of dissolving nobiletin or a nobiletin-comprising substance and a water-soluble hesperidin derivative selected from the group consisting of glucosyl hesperidin and methyl hesperidin in an ethanol aqueous solution having an ethanol concentration of from 20 to 90 vol % and a step of drying the solution.

<2> The method for producing a solid dispersion according to <1>, wherein nobiletin or the nobiletin-comprising substance and the water-soluble hesperidin derivative are dissolved in the ethanol aqueous solution at from 0 to 90° C.

<3> The method for producing a solid dispersion according to <1> or <2>, wherein an ethanol concentration of the ethanol aqueous solution is from 30 to 88 vol %.

<4> The method for producing a solid dispersion according to any of <1> to <3>, wherein a drying method is spray drying.

<5> The method for producing a solid dispersion according to any of <1> to <4>, wherein a mass ratio of nobiletin to the water-soluble hesperidin derivative [nobiletin/water-soluble hesperidin derivative], when nobiletin or the nobiletin-comprising substance and the water-soluble hesperidin derivative are mixed, is from 0.01 to 0.67.

<6> A nobiletin-comprising solid dispersion obtained by the method according to any of <1> to <5> and having a degree of crystallinity of nobiletin of 10% or less as calculated from an X-ray diffraction spectrum.

<7> A pharmaceutical product, a quasi-pharmaceutical product, or a cosmetic product comprising the nobiletin-comprising solid dispersion according to <6>.

<8> A food or drink comprising the nobiletin-comprising solid dispersion according to <6>.

<9> The food or drink according to <8>, being a solid instant food or drink eaten upon being dissolved in water or heated water when used and eaten.

<10> In <2>, a dissolution temperature is preferably 5° C. or more, and more preferably 10° C. or more, and preferably 85° C. or less, more preferably 80° C. or less, more preferably 75° C. or less, more preferably 70° C. or less, and more preferably 60° C. or less. Additionally, it is more preferably from 5 to 85° C., more preferably from 10 to 80° C., more preferably from 10 to 75° C., more preferably from 10 to 70° C., and more preferably from 10 to 60° C.

<11> In <3>, an ethanol concentration of the ethanol aqueous solution is more preferably 30 vol % or more, more preferably 35 vol % or more, more preferably 40 vol % or more, more preferably 50 vol % or more, more preferably 60 vol % or more, and more preferably 70 vol % or more, and more preferably 85 vol % or less, and more preferably 82 vol % or less. Additionally, it is more preferably from 30 to 85 vol %, more preferably from 35 to 85 vol %, more preferably from 40 to 82 vol %, and more preferably from 45 to 82 vol %.

<12> In <1>, a content of nobiletin in the mixture of nobiletin or the nobiletin-comprising substance and the water-soluble hesperidin derivative is preferably 1 mass % or more, more preferably 3 mass % or more, more preferably 4 mass % or more, more preferably 5 mass % or more, more preferably 7.5 mass % or more, more preferably 10 mass % or more, and more preferably 15 mass % or more, and preferably 90 mass % or less, more preferably 70 mass % or less, more preferably 60 mass % or less, more preferably 50 mass % or less, more preferably 45 mass % or less, more preferably 40 mass % or less, and more preferably 35 mass % or less, in the mixture. Additionally, it is preferably from 1 to 90 mass %, more preferably from 3 to 70 mass %, more preferably from 4 to 60 mass %, more preferably from 5 to 50 mass %, more preferably from 7.5 to 45 mass %, more preferably from 10 to 40 mass %, more preferably from 15 to 35 mass %, and more preferably 25 mass %.

<13> In <1>, a content of the water-soluble hesperidin derivative in the mixture of nobiletin or the nobiletin-comprising substance and the water-soluble hesperidin derivative is preferably 10 mass % or more, more preferably 20 mass % or more, more preferably 25 mass % or more, more preferably 30 mass % or more, more preferably 45 mass % or more, more preferably 60 mass % or more, and more preferably 65 mass % or more, and preferably 99 mass % or less, more preferably 97 mass % or less, more preferably 96 mass % or less, more preferably 92.5 mass % or less, more preferably 90 mass % or less, and more preferably 85 mass % or less, in the mixture. Additionally, it is preferably from 10 to 99 mass %, more preferably from 20 to 97 mass %, more preferably from 25 to 96 mass %, more preferably from 30 to 92.5 mass %, more preferably from 45 to 90 mass %, more preferably from 60 to 85 mass %, more preferably from 65 to 85 mass %, and more preferably 75 mass %.

<14> In <1>, a mass ratio of nobiletin to the water-soluble hesperidin derivative [nobiletin/water-soluble hesperidin derivative] when nobiletin or the nobiletin-comprising substance and the water-soluble hesperidin derivative are mixed is preferably 0.03 or more, more preferably 0.04 or more, more preferably 0.07 or more, and more preferably 0.1 or more, and preferably 9 or less, more preferably 4 or less, more preferably 3 or less, more preferably 1 or less, and more preferably 0.67 or less. Additionally, it is preferably from 0.01 to 9, more preferably from 0.03 to 4, more preferably from 0.04 to 3, more preferably from 0.07 to 1, more preferably from 0.1 to 0.67, and more preferably 0.33.

<15> In <1>, a degree of crystallinity of nobiletin is preferably 50% or less, more preferably 40% or less, more preferably 20% or less, more preferably 10% or less, more preferably 5% or less, and more preferably 0%.

EXAMPLE

[Quantitative Determination of Poorly Water-Soluble Substance]

High-performance liquid chromatography (HPLC) was used to quantify poorly water-soluble polyphenols. For the detection, an ultraviolet-visible spectroscopy (UV-vis) detector or a mass spectrometer (MS/MS) was used.

[Quantitative Determination of Poorly Water-Soluble Substance by HPLC-UV-Vis]

Quantitative determination was carried out by the gradient method using Agilent Technologies, Inc. high-performance liquid chromatograph with a Chemicals Evaluation and Research Institute column L-Column ODS-2 (4.6 mmφ×50 mm, 2 μm) attached at a column temperature of 40° C.

A sample injection volume was 10 μL, mobile phase liquid A was a 0.1 wt % trifluoroacetic acid aqueous solution, liquid B was acetonitrile, and solution sending was 1.0 mL/min. Gradient conditions are as follows.

| Time (min.) | Liquid A (%) | Liquid B (%) |
| --- | --- | --- |
| 0 | 99 | 1 |
| 1 | 99 | 1 |
| 4 | 5 | 95 |
| 5 | 5 | 95 |
| 5.01 | 99 | 1 |
| 6 | 99 | 1 |

For the detection, nobiletin was quantified with absorbance at a wavelength of 320 nm and ellagic acid was quantified with absorbance at a wavelength of 254 nm.

[Quantitative Determination of Poorly Water-Soluble Substance by HPLC-UV-Vis]

Quantitative determination was carried out by the gradient method using Agilent Technologies, Inc. high-performance liquid chromatograph with a Chemicals Evaluation and Research Institute column L-Column ODS-2 (4.6 mmφ×50 mm, 2 μm) attached at a column temperature of 40° C.

For nobiletin measurement, a sample injection volume was 10 μL, mobile phase liquid A was a 0.1 wt % formic acid aqueous solution, liquid B was acetonitrile, and solution sending was 0.6 mL/min. Gradient conditions are as follows.

| Time (min) | Liquid A (%) | Liquid B (%) |
| --- | --- | --- |
| 0 | 90 | 10 |
| 0.5 | 90 | 10 |
| 4 | 10 | 90 |
| 5 | 10 | 90 |
| 5.01 | 90 | 10 |
| 6 | 90 | 10 |

For ellagic acid measurement, a sample injection volume was 10 μL, mobile phase liquid A was a 5.0 wt % formic acid aqueous solution, liquid B was acetonitrile, and solution sending was 0.6 mL/min. Gradient conditions are as follows.

| Time (min) | Liquid A (%) | Liquid B (%) |
| --- | --- | --- |
| 0 | 99 | 1 |
| 0.5 | 99 | 1 |
| 4 | 5 | 95 |
| 5 | 5 | 95 |
| 5.01 | 99 | 1 |
| 6 | 99 | 1 |

[MS/MS Conditions]

QTRAP®4500 (manufactured by AB Sciex Pte. Ltd.) was used as a mass spectrometer. Scan condition was MRM and parameter table was measured by Analight. For the quantification, nobiletin ions were detected at MRM (m/Z) 404.0→374.0 in the positive ion mode and ellagic acid ions were detected at MRM (m/Z) 300.9→284.0 in the negative mode, respectively.

[X-Ray Diffractometry]

An X-ray diffraction intensity was measured using "Mini Flex II" manufactured by Rigaku Corporation under conditions of X-ray source: Cu/Kα-radiation, tube voltage: 30 kV, tube current: 15 mA, measurement range: diffraction angle: from 5 to 40°, and X-ray scan speed: 10°/min. Measurement samples were manufactured by compressing pellets having an area of 400 mm²×a thickness of 0.5 mm.

[Evaluation on Time-Course Solubility]

Thirty mL of ion exchange water was added to a 50-mL screw vial (manufactured by Maruemu Corporation, No. 2, brown), then 100 mg of the solid dispersion was added, and the resulting mixture was stirred using a 2-cm stirrer chip at 500 rpm. During 6 hours of stirring with the start of stirring being 0 minutes, a part of the mixture was suitably filtered using a 0.45 µm cellulose acetate filter and amounts of nobiletin and ellagic acid dissolved were quantified by the method described in the [Quantitative determination of poorly water-soluble substance].

[Caco-2 Cell Membrane Permeability Evaluation]

Test Example 1 Permeation Promotion Test on Poorly Water-Soluble Substance Active Pharmaceutical Ingredient and Solid Dispersion Thereof Through the Small Intestinal Epithelium Using Human Epithelial Colorectal Adenocarcinoma Cells Caco-2 cells (human epithelial colorectal adenocarcinoma cells, obtained from DS Pharma Biochemical Co., Ltd.) were cultured at 37° C. in the presence of 5% $CO_2$. For the culture, a Caco-2 cell differentiation medium set (manufactured by Corning Incorporated) and a BioCoat Fibrillar Collagen HTS multiwell insert (24 wells, membrane pore 1 µm, manufactured by Corning Incorporated) were used. Caco-2 cells were suspended in seeding basal medium to which MITO+™Serum Extender was added and seeded in the upper portion of an insert (apical membrane side) and the same medium was also added to the lower portion of an insert (basolateral membrane side). After 24-hour culture of Caco-2 cells, the seeding basal medium was replaced with Entero-STIM Intestinal Epithelium Differentiation Medium to which MITO+™Serum Extender was added. Subsequently, the cells were further cultured for 48 hours and differentiated into intestinal epithelium cell sheets.

For confirming the formation of tight junctions of the intestines, transepithelial electrical resistance (TEER) value was measured using Millicell ERS (manufactured by Millipore) immediately before the permeation promotion test on poorly water-soluble substance active pharmaceutical ingredient and solid dispersion thereof through the small intestine epithelium, and Caco-2 cells having a defined value (350 $\Omega \cdot cm^2$) or more were used.

Preparation of evaluation samples was carried out as follows. Six mL of HBSS (manufactured by Invitrogen, 10 mM MES, 5 mM glucose, 10 mM glutamine, and 1 mM ascorbic acid were added and pH was adjusted to 6.0) was added to a 20-mL screw vial (manufactured by Maruemu Corporation, No. 2, brown), then 10 mg of the poorly water-soluble active pharmaceutical ingredient or 40 mg of the solid dispersion was added and stirred for 10 minutes using a 2-cm stirrer chip at 300 rpm. After stirring, the solution filtered using a 0.45 µm cellulose acetate filter and a dilute solution thereof were used as evaluation samples. Table 1-1 to Table 1-4 show the results of evaluations in which the solution obtained by diluting the filtrate 30 folds with HBSS was used as the insert upper portion preparation solution.

After cell selection by the TEER measurement, the upper and lower portion of the insert were replaced with HBSS and washed twice. Subsequently, the dilute solutions of the poorly water-soluble substance and the solid dispersion aqueous solution thereof prepared by the above method were added to the upper portion of the insert. Tables 1-1 to 1-4 show the evaluated concentrations of the dilutions. HBSS (10 mM HEPES, 5 mM glucose, 10 mM glutamine, pH 7.4) was added to the lower portion of the insert. Then, Caco-2 cells were cultured at 37° C. in the presence of 5% $CO_2$ for 4 hours.

Subsequently, the HBSS at the lower portion of the insert was collected and the poorly water-soluble substance permeated through the intestinal epithelium was quantified by the following method using the liquid chromatography•tandem mass spectrometry (HPLC-MS/MS).

[Cell Viability Evaluation by LDH Activity Measurement Test]

Test Example 2 LDH Activity Measurement Test

The HBSS at the upper portion of the insert of Test Example 1 was collected and a cell viability was evaluated by the following method from the cytotoxicity of each evaluation sample determined from LDH (Lactate dehydrogenase) activity measurement in the solution released from the Caco-2 cells making up the cell membrane.

The evaluation of the cytotoxicity was carried out by a prescribed method using an LDH Cytotoxicity Assay Kit (manufactured by Cayman Chemical Company). Using the test solution at the upper portion of the insert after completing the evaluation as a sample, LDH activity was calculated from an amount of formazan produced by LDH contained (quantified from absorption intensity at 490 nm). For the calculation of cell viability, the LDH activity of the test solution at the upper portion of the insert after completing the evaluation was defined as a value equivalent to 0% of cell viability when a solution of 1.0% Triton X-100 in HESS was used as a sample for Caco-2 cell membrane permeability evaluation (Test Example 1). Then, a fold change of the LDH activity was calculated by the following formula.

Cell viability (%)=(LDH activity of the test solution at the upper portion of the insert after completing the evaluation of 1.0% Triton $X$ HESS solution−LDH activity of the test solution at the upper portion of the insert after completing the evaluation of each sample)÷(LDH activity of the test solution at the upper portion of the insert after completing the evaluation of 1.0% Triton $X$ HBSS solution)     (Calculation formula)

Table 1 shows an average value and a standard error (N=3 or 4) of the cell viability results determined by the calculation formula.

Example 1

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 76° C., a solution supply speed: 360 mL/h, a spray nitrogen flow rate: 414 L/h, and an aspirator flow rate: 35 $m^3$/h to prepare a solid dispersion. The obtained solid dispersion was 1.73 g (yield 35%).

Figure 2:
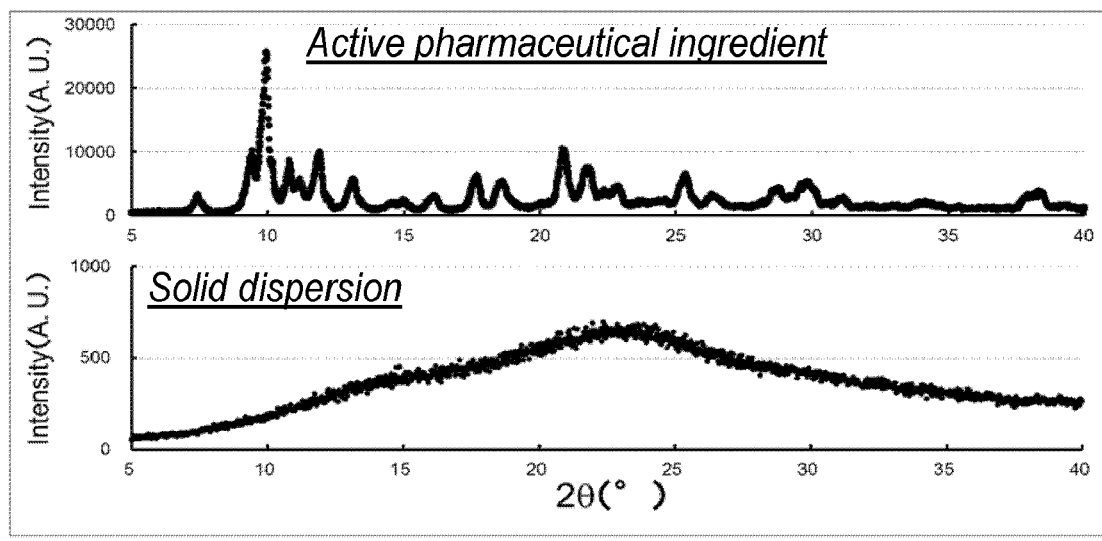
FIG. 2 shows powder X-ray diffraction results of nobiletin (upper figure) and nobiletin-methyl hesperidin solid dispersion (lower figure) of Example 1.

A powder X-ray diffraction of the solid dispersion is shown in FIG. 2. Loss of diffraction peaks derived from nobiletin confirms the amorphization of nobiletin in the solid dispersion, and the degree of crystallinity of the solid dispersion was estimated as 0%.

Dissolved concentration of nobiletin in the solid dispersion was measured by the above [Evaluation on time-course solubility] and consequently it was found that the area under the curve from the start of stirring up to 6 hours later (horizontal axis: time (unit=min), vertical axis: dissolved concentration (unit=ppm)) was $1.13 \times 10^5$ ppm-min and extremely high dissolved concentration was retained for a long time (FIG. 1 and Table 1-1).

Additionally, when the solid dispersion was tested by the above [Caco-2 cell membrane permeability evaluation], the nobiletin concentration at the time of starting evaluation of the upper portion of the insert was 41.8 μM and the nobiletin concentration at the time of completing evaluation of the lower portion of the insert was 1.08 μM, which confirms the enhancement in the amount of nobiletin permeating through the membrane due to the high solubility (Table 1-1).

Example 2

Two point five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 76° C., a solution supply speed: 360 mL/h, a spray nitrogen flow rate: 414 L/h, and an aspirator flow rate: 35 $m^3$/h to prepare a solid dispersion. The obtained solid dispersion was 0.75 g (yield 30%).

Figure 3:
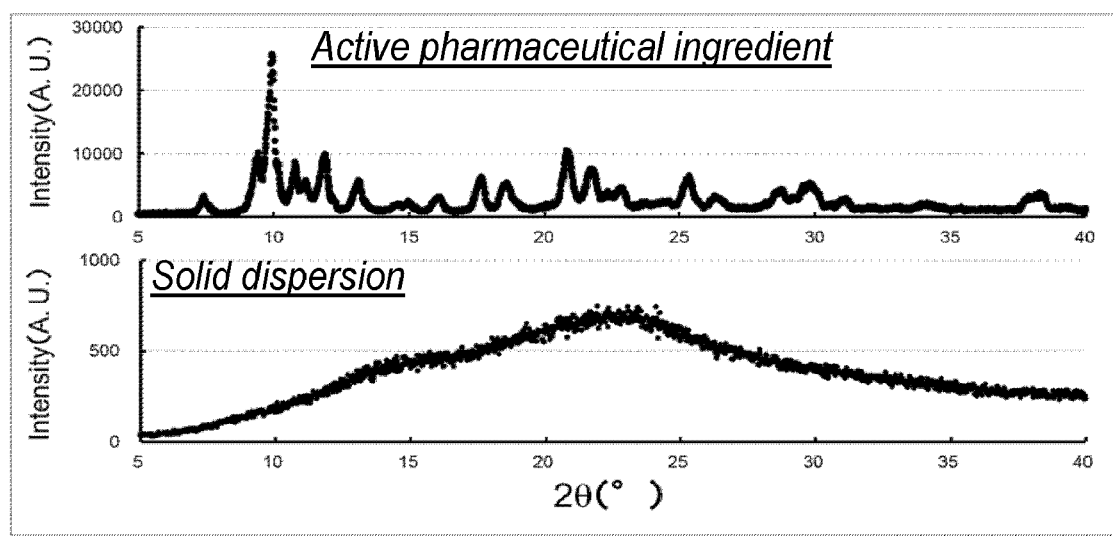
FIG. 3 shows powder X-ray diffraction results of nobiletin (upper figure) and nobiletin-methyl hesperidin solid dispersion (lower figure) of Example 2.

A powder X-ray diffraction of the solid dispersion is shown in FIG. 3. As in Example 1, the amorphization of nobiletin in the solid dispersion was confirmed. The results of the above [Evaluation on time-course solubility] and [Caco-2 cell membrane permeability evaluation] are shown in Table 1-1.

Example 3

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 80 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 78° C., a solution supply speed: 360 mL/h, a spray nitrogen flow rate: 414 L/h, and an aspirator flow rate: 35 $m^3$/h to prepare a solid dispersion. The obtained solid dispersion was 2.17 g (yield 43%).

Figure 4:
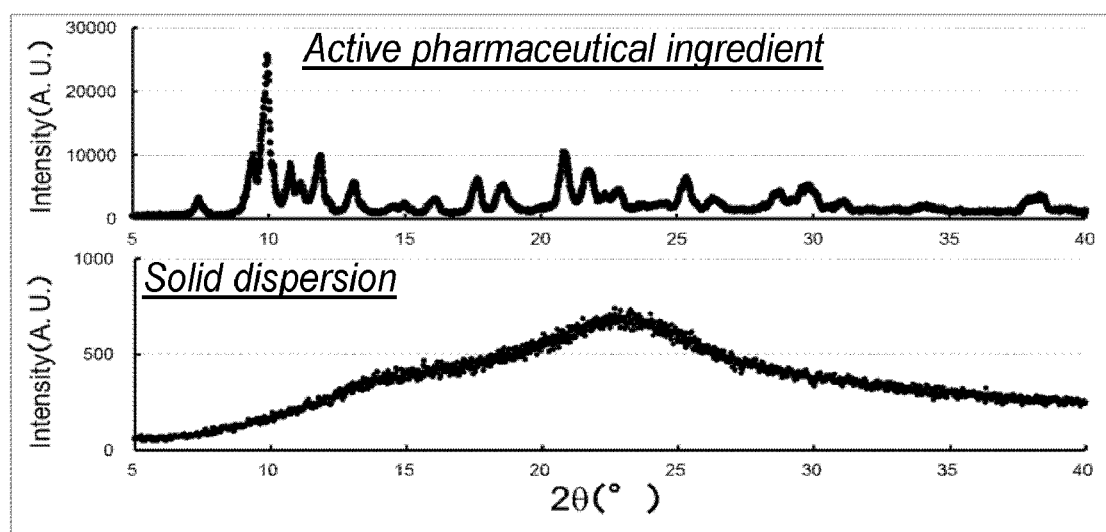
FIG. 4 shows powder X-ray diffraction results of nobiletin (upper figure) and nobiletin-methyl hesperidin solid dispersion (lower figure) of Example 3.

A powder X-ray diffraction of the solid dispersion is shown in FIG. 4. As in Example 1, the amorphization of nobiletin in the solid dispersion was confirmed. The results of the above [Evaluation on time-course solubility] and [Caco-2 cell membrane permeability evaluation] are shown in Table 1-1.

Example 4

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 110° C., an outlet gas temperature: 60° C., a solution supply speed: 360 mL/h, a spray nitrogen flow rate: 414 L/h, and an aspirator flow rate: 35 $m^3$/h to prepare a solid dispersion. The obtained solid dispersion was 2.32 g (yield 46%).

Figure 5:
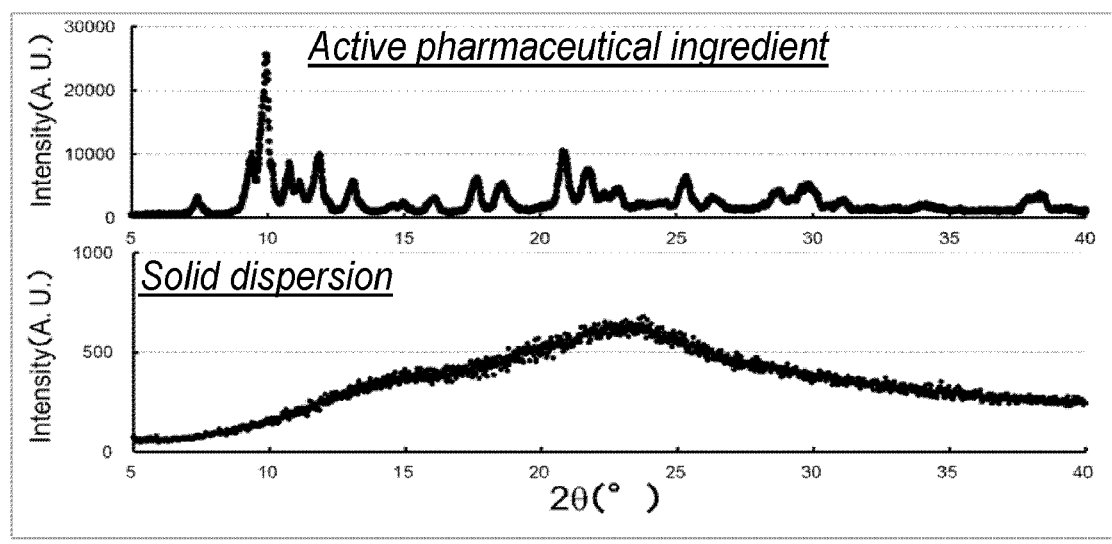
FIG. 5 shows powder X-ray diffraction results of nobiletin (upper figure) and nobiletin-methyl hesperidin solid dispersion (lower figure) of Example 4.

A powder X-ray diffraction of the solid dispersion is shown in FIG. 5. As in Example 1, the amorphization of nobiletin in the solid dispersion was confirmed. The results of the above [Evaluation on time-course solubility] and [Caco-2 cell membrane permeability evaluation] are shown in Table 1-1.

Example 5

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 95 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 76° C., a solution supply speed: 360 mL/h, a spray nitrogen flow rate: 414 L/h, and an aspirator flow rate: 35 $m^3$/h to prepare a solid dispersion. The obtained solid dispersion was 3.27 g (yield 65%).

Figure 6:
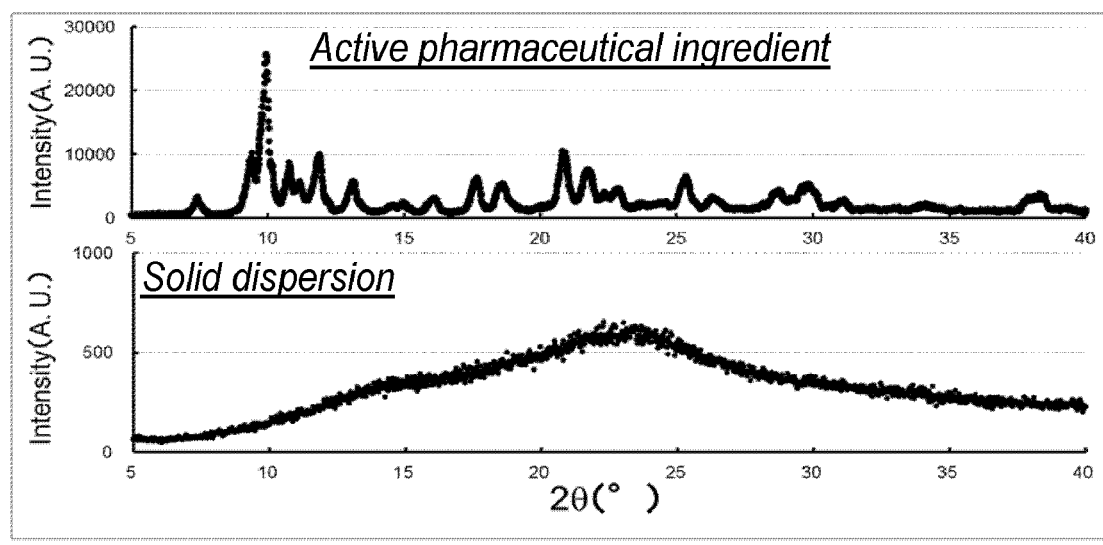
FIG. 6 shows powder X-ray diffraction results of nobiletin (upper figure) and nobiletin-methyl hesperidin solid dispersion (lower figure) of Example 5.

A powder X-ray diffraction of the solid dispersion is shown in FIG. 6. As in Example 1, the amorphization of nobiletin in the solid dispersion was confirmed. The results of the above [Evaluation on time-course solubility] and [Caco-2 cell membrane permeability evaluation] are shown in Table 1-1.

Example 6

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 20 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 74° C., a solution supply speed: 360 mL/h, a spray nitrogen flow rate: 414 L/h, and an aspirator flow rate: 35 $m^3$/h to prepare a solid dispersion. The obtained solid dispersion was 2.79 g (yield 56%).

Figure 7:
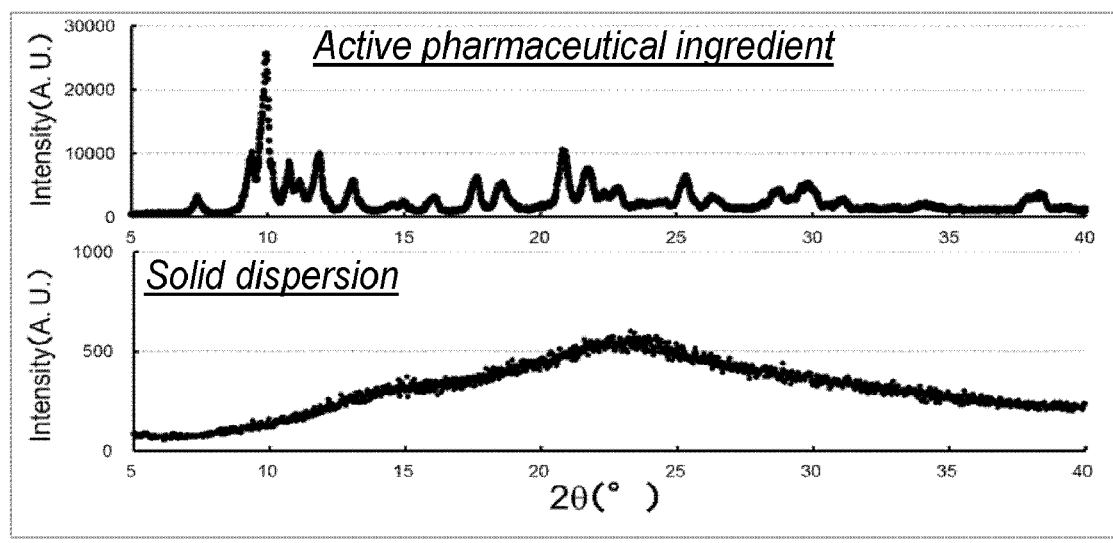
FIG. 7 shows powder X-ray diffraction results of nobiletin (upper figure) and nobiletin-methyl hesperidin solid dispersion (lower figure) of Example 6.

A powder X-ray diffraction of the solid dispersion is shown in FIG. 7. As in Example 1, the amorphization of nobiletin in the solid dispersion was confirmed. The results of the above [Evaluation on time-course solubility] and [Caco-2 cell membrane permeability evaluation] are shown in Table 1-1.

Example 7

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 77° C., a solution supply speed: 180 mL/h, a spray nitrogen flow rate: 414 L/h, and an aspirator flow rate: 35 m³/h to prepare a solid dispersion. The obtained solid dispersion was 1.25 g (yield 25%).

Figure 8:
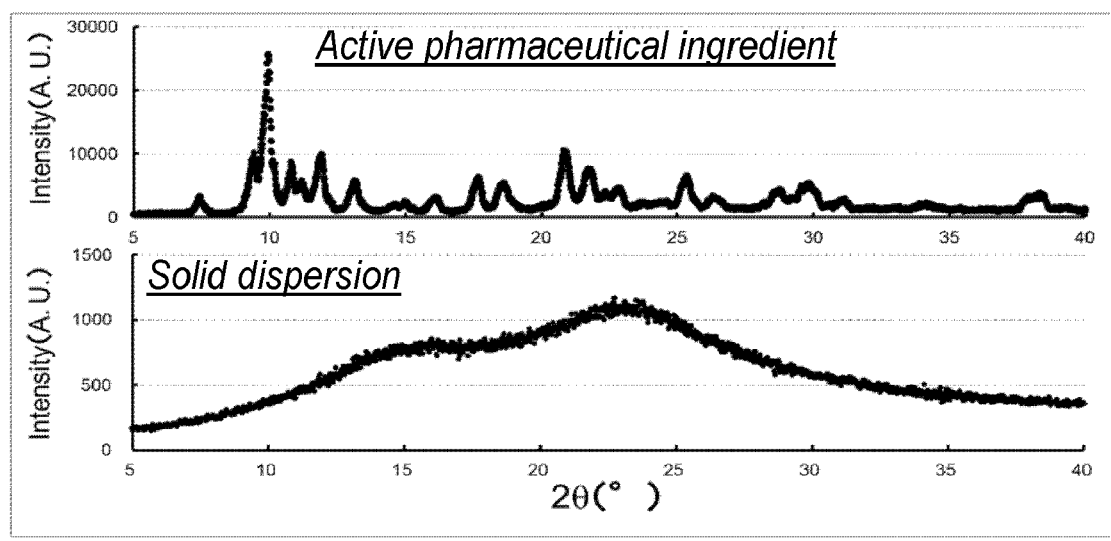
FIG. 8 shows powder X-ray diffraction results of nobiletin (upper figure) and nobiletin-methyl hesperidin solid dispersion (lower figure) of Example 7.

A powder X-ray diffraction of the solid dispersion is shown in FIG. 8. As in Example 1, the amorphization of nobiletin in the solid dispersion was confirmed. The results of the above [Evaluation on time-course solubility] and [Caco-2 cell membrane permeability evaluation] are shown in Table 1-1.

Example 8

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 77° C., a solution supply speed: 360 mL/h, a spray nitrogen flow rate: 207 L/h, and an aspirator flow rate: 35 m³/h to prepare a solid dispersion. The obtained solid dispersion was 0.23 g (yield 5%).

Figure 9:
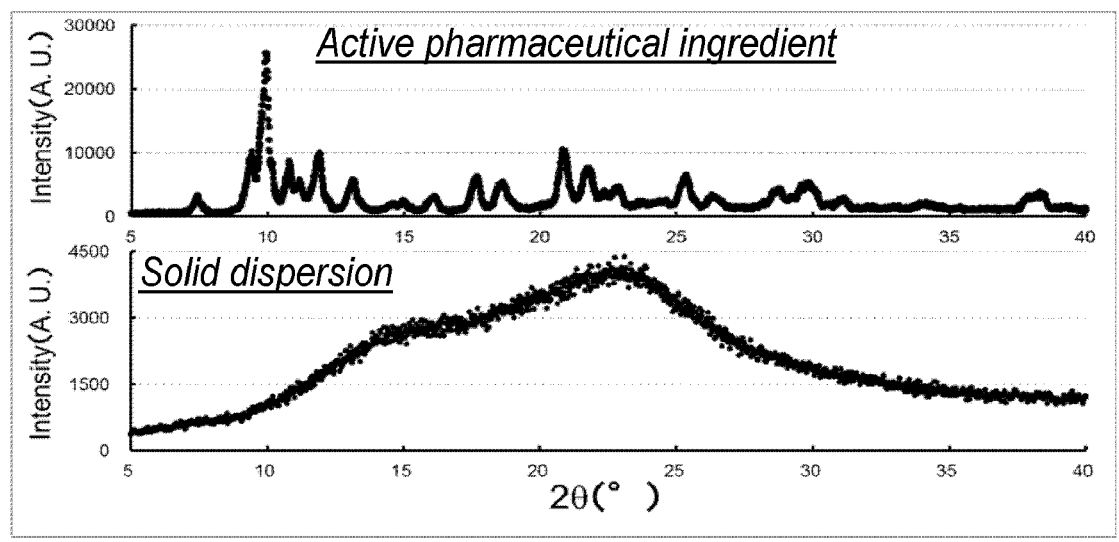
FIG. 9 shows powder X-ray diffraction results of nobiletin (upper figure) and nobiletin-methyl hesperidin solid dispersion (lower figure) of Example 8.

A powder X-ray diffraction of the solid dispersion is shown in FIG. 9. As in Example 1, the amorphization of nobiletin in the solid dispersion was confirmed. The results of the above [Evaluation on time-course solubility] and [Caco-2 cell membrane permeability evaluation] are shown in Table 1-1.

Example 9

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 73° C., a solution supply speed: 540 mL/h, a spray nitrogen flow rate: 414 L/h, and an aspirator flow rate: 35 m³/h to prepare a solid dispersion. The obtained solid dispersion was 1.26 g (yield 25%).

Figure 10:
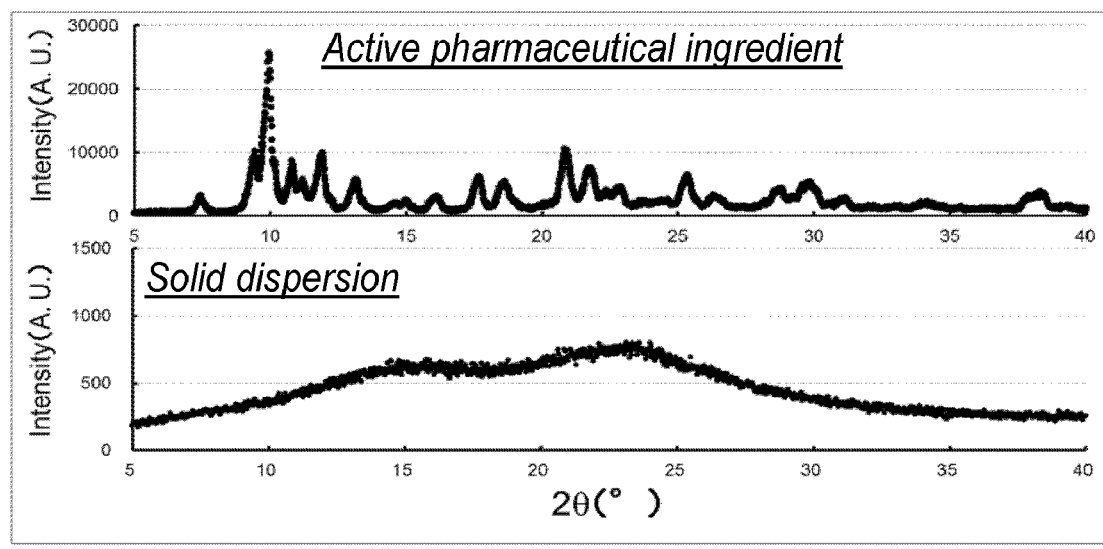
FIG. 10 shows powder X-ray diffraction results of nobiletin (upper figure) and nobiletin-methyl hesperidin solid dispersion (lower figure) of Example 9.

A powder X-ray diffraction of the solid dispersion is shown in FIG. 10. As in Example 1, the amorphization of nobiletin in the solid dispersion was confirmed. The results of the above [Evaluation on time-course solubility] and [Caco-2 cell membrane permeability evaluation] are shown in Table 1-2.

Example 10

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 70° C., a solution supply speed: 360 mL/h, a spray nitrogen flow rate: 621 L/h, and an aspirator flow rate: 35 m³/h to prepare a solid dispersion. The obtained solid dispersion was 0.62 g (yield 12%).

Figure 11:
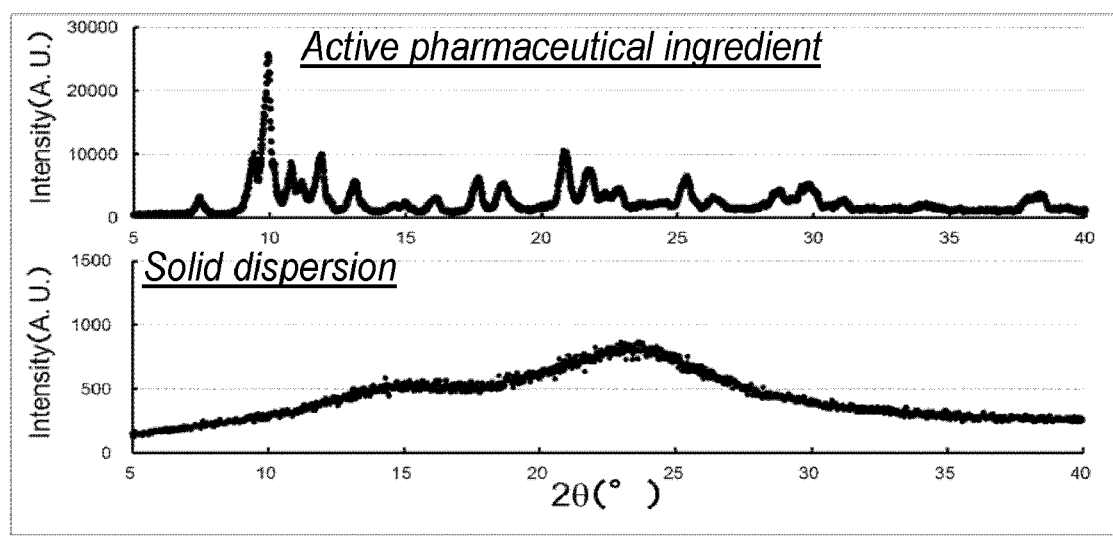
FIG. 11 shows powder X-ray diffraction results of nobiletin (upper figure) and nobiletin-methyl hesperidin solid dispersion (lower figure) of Example 10.

A powder X-ray diffraction of the solid dispersion is shown in FIG. 11. As in Example 1, the amorphization of nobiletin in the solid dispersion was confirmed. The results of the above [Evaluation on time-course solubility] and [Caco-2 cell membrane permeability evaluation] are shown in Table 1-2.

Example 11

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 10 mass % to 90 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 71° C., a solution supply speed: 360 mL/h, a spray nitrogen flow rate: 414 L/h, and an aspirator flow rate: 35 m³/h to prepare a solid dispersion. The obtained solid dispersion was 2.46 g (yield 49%).

Figure 12:
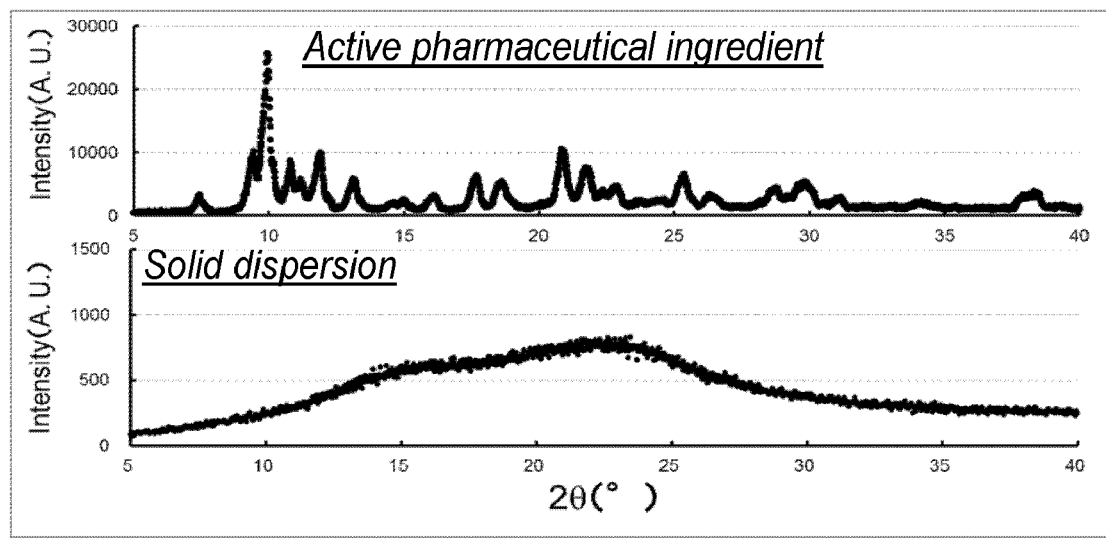
FIG. 12 shows powder X-ray diffraction results of nobiletin (upper figure) and nobiletin-methyl hesperidin solid dispersion (lower figure) of Example 11.

A powder X-ray diffraction of the solid dispersion is shown in FIG. 12. As in Example 1, the amorphization of nobiletin in the solid dispersion was confirmed. The results of the above [Evaluation on time-course solubility] and [Caco-2 cell membrane permeability evaluation] are shown in Table 1-2.

Example 12

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 50 mass % to 50 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 72° C., a solution supply speed: 360 mL/h, a spray nitrogen flow rate: 414 L/h, and an aspirator flow rate: 35 m³/h to prepare a solid dispersion. The obtained solid dispersion was 0.59 g (yield 12%).

Figure 13:
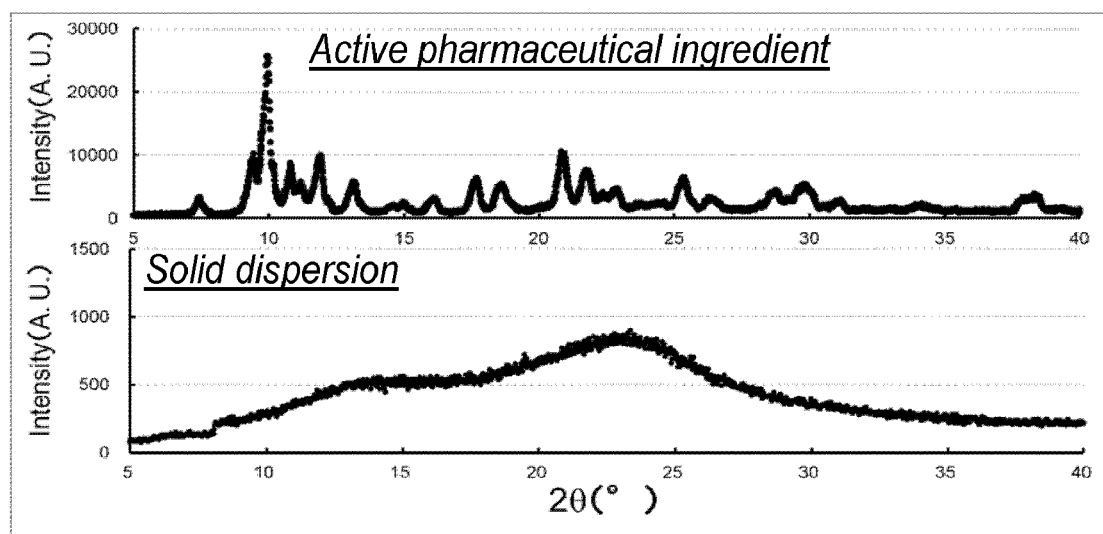
FIG. 13 shows powder X-ray diffraction results of nobiletin (upper figure) and nobiletin-methyl hesperidin solid dispersion (lower figure) of Example 12.

A powder X-ray diffraction of the solid dispersion is shown in FIG. 13. As in Example 1, the amorphization of nobiletin in the solid dispersion was confirmed. The results of the above [Evaluation on time-course solubility] and [Caco-2 cell membrane permeability evaluation] are shown in Table 1-2.

Example 13

Five g of a powder in which nobiletin (manufactured by Wako Pure Chemical Industries, Ltd.) and methyl hesperidin (manufactured by Tokyo Chemical Industry Co., Ltd.) were mixed respectively in a ratio of 40 mass % to 60 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 76° C., a solution supply speed: 360 mL/h, a spray nitrogen flow rate: 414 L/h, and an aspirator flow rate: 35 m$^3$/h to prepare a solid dispersion. The obtained solid dispersion was 1.95 g (yield 39%).

Figure 14:
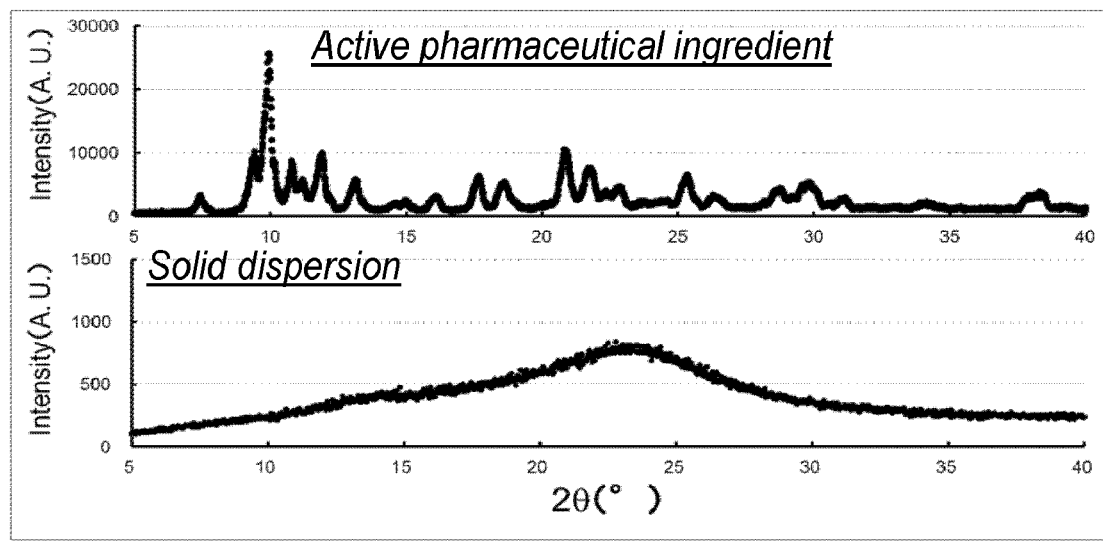
FIG. 14 shows powder X-ray diffraction results of nobiletin (upper figure) and nobiletin-methyl hesperidin solid dispersion (lower figure) of Example 13.

A powder X-ray diffraction of the solid dispersion is shown in FIG. 14. As in Example 1, the amorphization of nobiletin in the solid dispersion was confirmed. The results of the above [Evaluation on time-course solubility] and [Caco-2 cell membrane permeability evaluation] are shown in Table 1-2.

Example 14

Five g of a powder (containing 14 mass % nobiletin) in which PMF90 (manufactured by Okinawa Research Center, nobiletin content ratio of 56% (quantitative value by HPLC-UV-vis, conducted by Kao Corporation)) and methyl hesperidin (manufactured by Tokyo Chemical Industry Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 78° C., a solution supply speed: 360 mL/h, a spray nitrogen flow rate: 414 L/h, and an aspirator flow rate: 35 m$^3$/h to prepare a solid dispersion. The obtained solid dispersion was 1.18 g (yield 24%).

Figure 15:
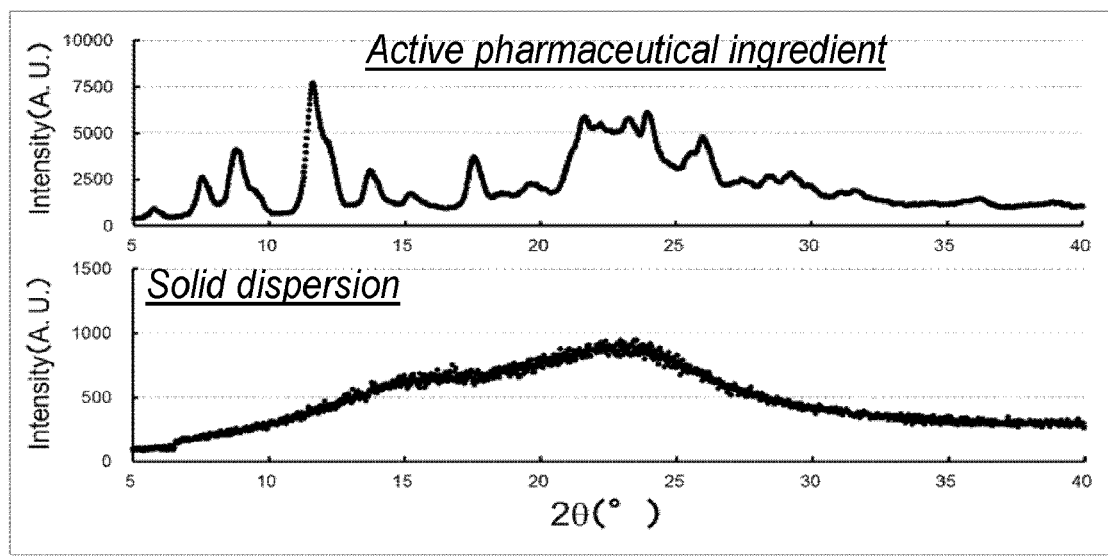
FIG. 15 shows powder X-ray diffraction results of PMF90 (upper figure) and PMF90-methyl hesperidin solid dispersion (lower figure) of Example 14.

A powder X-ray diffraction of the solid dispersion is shown in FIG. 15. As in Example 1, the amorphization of nobiletin in the solid dispersion was confirmed. The results of the above [Evaluation on time-course solubility] and [Caco-2 cell membrane permeability evaluation] are shown in Table 1-2.

Example 15

Five g of a powder (containing 28 mass % nobiletin) in which PMF90 (manufactured by Okinawa Research Center) and methyl hesperidin (manufactured by Tokyo Chemical Industry Co., Ltd.) were mixed respectively in a ratio of 50 mass % to 50 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 78° C., a solution supply speed: 360 mL/h, a spray nitrogen flow rate: 414 L/h, and an aspirator flow rate: 35 m$^3$/h to prepare a solid dispersion. The obtained solid dispersion was 0.13 g (yield 3%).

Figure 16:
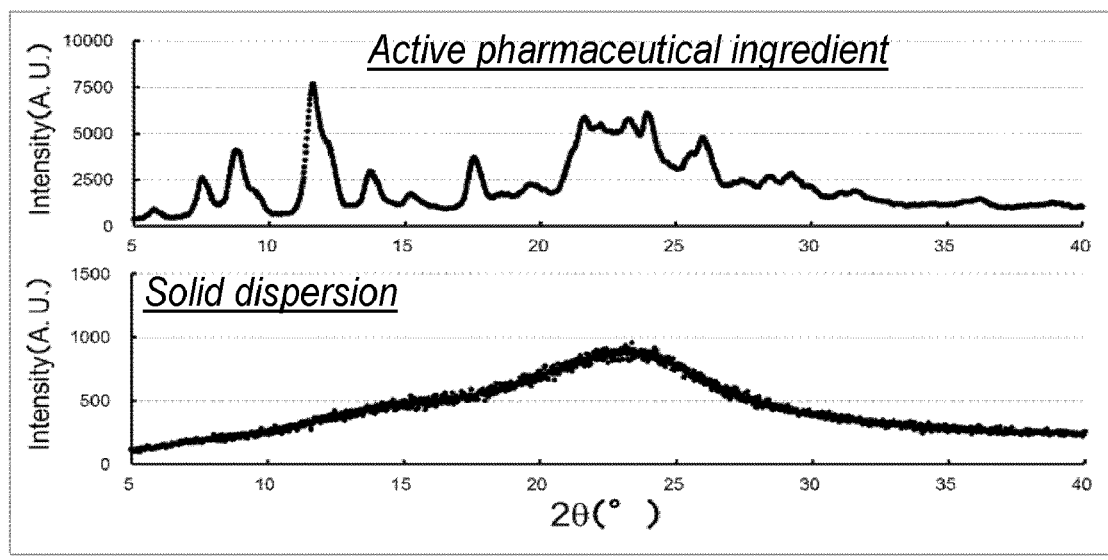
FIG. 16 shows powder X-ray diffraction results of PMF90 (upper figure) and PMF90-methyl hesperidin solid dispersion (lower figure) of Example 15.

A powder X-ray diffraction of the solid dispersion is shown in FIG. 16. As in Example 1, the amorphization of nobiletin in the solid dispersion was confirmed. The results of the above [Evaluation on time-course solubility] and [Caco-2 cell membrane permeability evaluation] are shown in Table 1-2.

Example 16

Five g of a powder (containing 22 mass % nobiletin) in which PMF90 (manufactured by Okinawa Research Center) and methyl hesperidin (manufactured by Tokyo Chemical Industry Co., Ltd.) were mixed respectively in a ratio of 40 mass % to 60 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 77° C., a solution supply speed: 360 mL/h, a spray nitrogen flow rate: 414 L/h, and an aspirator flow rate: 35 m$^3$/h to prepare a solid dispersion. The obtained solid dispersion was 1.7 g (yield 34%).

Figure 17:
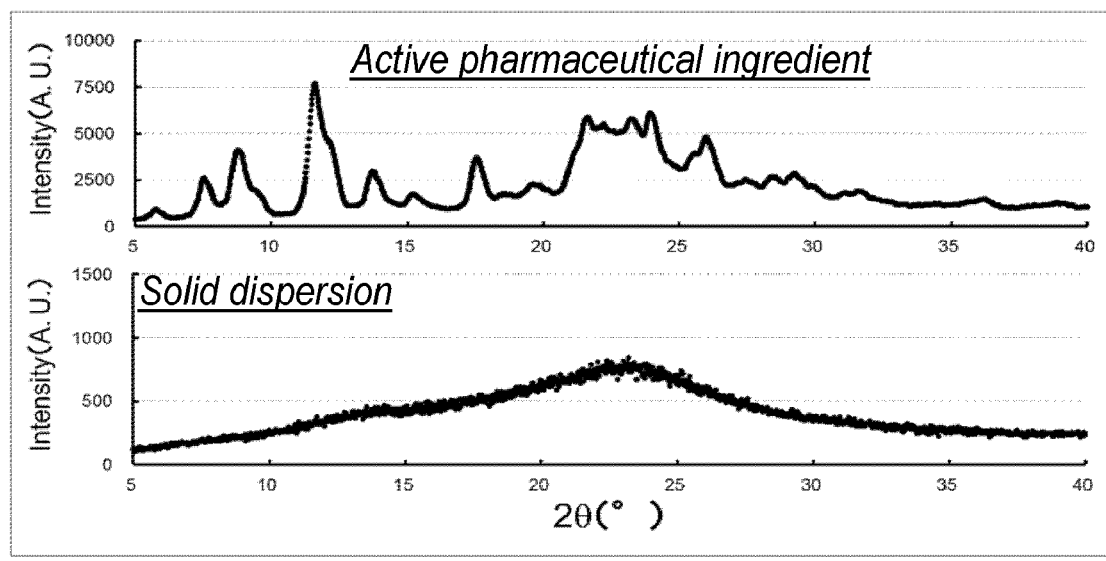
FIG. 17 shows powder X-ray diffraction results of PMF90 (upper figure) and PMF90-methyl hesperidin solid dispersion (lower figure) of Example 16.

A powder X-ray diffraction of the solid dispersion is shown in FIG. 17. As in Example 1, the amorphization of nobiletin in the solid dispersion was confirmed. The results of the above [Evaluation on time-course solubility] and [Caco-2 cell membrane permeability evaluation] are shown in Table 1-2.

Example 17

Five g of a powder in which nobiletin (manufactured by Wako Pure Chemical Industries, Ltd.) and αG hesperidin PA-T (manufactured by Toyo Sugar Refining Co., Ltd.) were mixed respectively in a ratio of 25 mass % to 75 mass % was mixed with 50 mL of water containing 80 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 74° C., a solution supply speed: 360 mL/h, a spray nitrogen flow rate: 414 L/h, and an aspirator flow rate: 35 m$^3$/h to prepare a solid dispersion. The obtained solid dispersion was 1.33 g (yield 27%).

Figure 18:
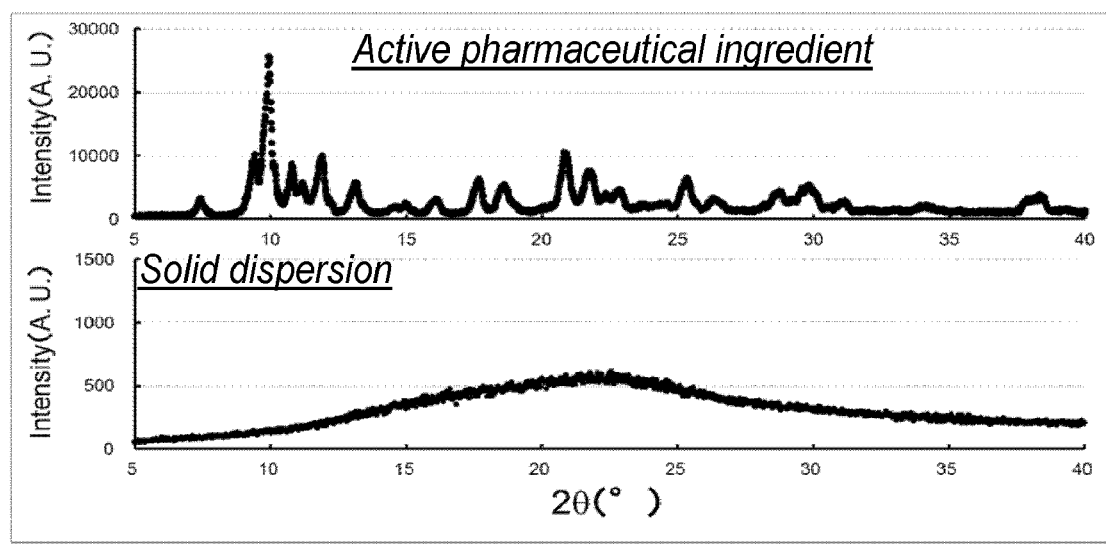
FIG. 18 shows powder X-ray diffraction results of nobiletin (upper figure) and nobiletin-αG hesperidin PA-T solid dispersion (lower figure) of Example 17.

A powder X-ray diffraction of the solid dispersion is shown in FIG. 18. As in Example 1, the amorphization of nobiletin in the solid dispersion was confirmed. The results of the above [Evaluation on time-course solubility] and [Caco-2 cell membrane permeability evaluation] are shown in Table 1-3.

Example 18

Five g of a powder in which nobiletin (manufactured by Wako Pure Chemical Industries, Ltd.) and αG hesperidin PA-T (manufactured by Toyo Sugar Refining Co., Ltd.) were mixed respectively in a ratio of 25 mass % to 75 mass % was mixed with 50 mL of water containing 80 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 110° C., an outlet gas temperature: 66° C., a solution supply speed: 360 mL/h, a spray nitrogen flow rate: 414 L/h, and an aspirator flow rate: 35 m$^3$/h to prepare a solid dispersion. The obtained solid dispersion was 1.81 g (yield 36%).

Figure 19:
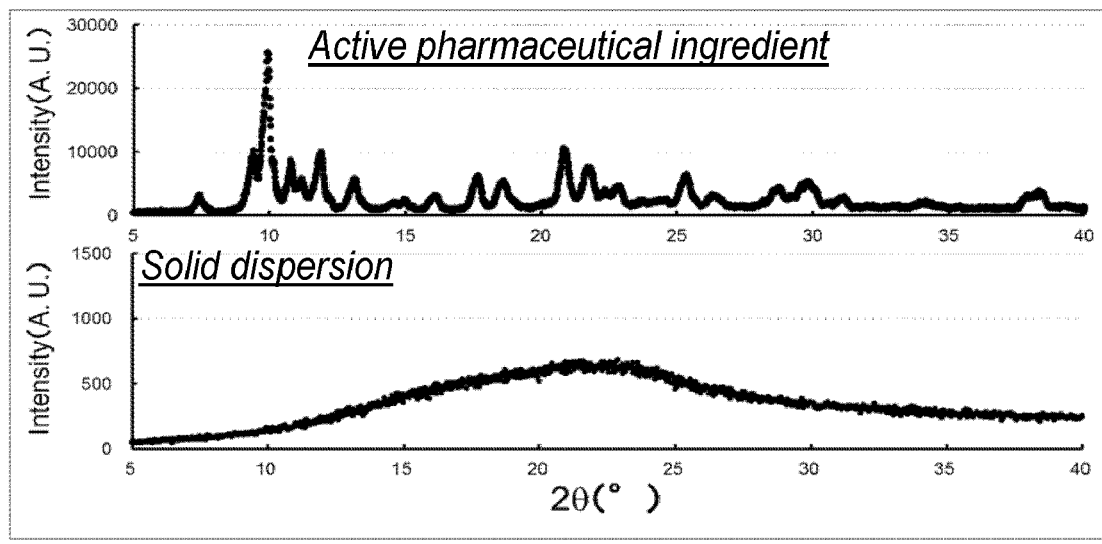
FIG. 19 shows powder X-ray diffraction results of nobiletin (upper figure) and nobiletin-αG hesperidin PA-T solid dispersion (lower figure) of Example 18.

A powder X-ray diffraction of the solid dispersion is shown in FIG. 19. As in Example 1, the amorphization of nobiletin in the solid dispersion was confirmed. The results of the above [Evaluation on time-course solubility] and [Caco-2 cell membrane permeability evaluation] are shown in Table 1-3.

Example 19

Five g of a powder in which nobiletin (manufactured by Wako Pure Chemical Industries, Ltd.) and αG hesperidin PA-T (manufactured by Toyo Sugar Refining Co., Ltd.) were mixed respectively in a ratio of 40 mass % to 60 mass % was mixed with 50 mL of water containing 80 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 78° C., a solution supply speed: 360 mL/h, a spray nitrogen flow rate: 414 L/h, and an aspirator flow rate: 35 m$^3$/h to prepare a solid dispersion. The obtained solid dispersion was 1.33 g (yield 27%).

Figure 20:
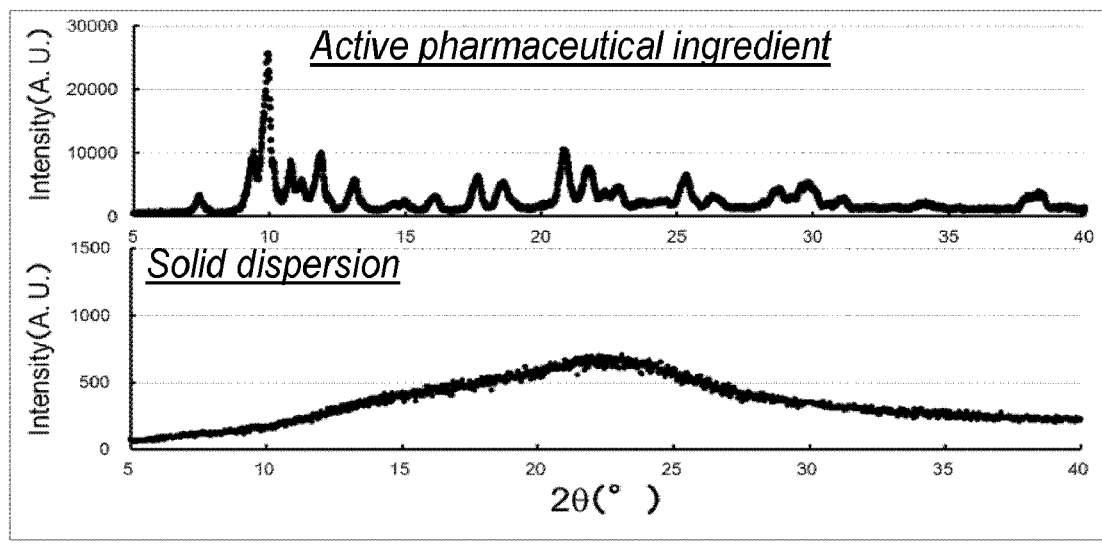
FIG. 20 shows powder X-ray diffraction results of nobiletin (upper figure) and nobiletin-αG hesperidin PA-T solid dispersion (lower figure) of Example 19.

A powder X-ray diffraction of the solid dispersion is shown in FIG. 20. As in Example 1, the amorphization of nobiletin in the solid dispersion was confirmed. The results of the above [Evaluation on time-course solubility] and [Caco-2 cell membrane permeability evaluation] are shown in Table 1-3.

Example 20

Five g of a powder in which nobiletin (manufactured by Wako Pure Chemical Industries, Ltd.) and αG hesperidin PA-T (manufactured by Toyo Sugar Refining Co., Ltd.) were mixed respectively in a ratio of 25 mass % to 75 mass % was mixed with 50 mL of water containing 50 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 78° C., a solution supply speed: 360 mL/h, a spray nitrogen flow rate: 414 L/h, and an aspirator flow rate: 35 m$^3$/h to prepare a solid dispersion. The obtained solid dispersion was 1.46 g (yield 29%).

Figure 21:
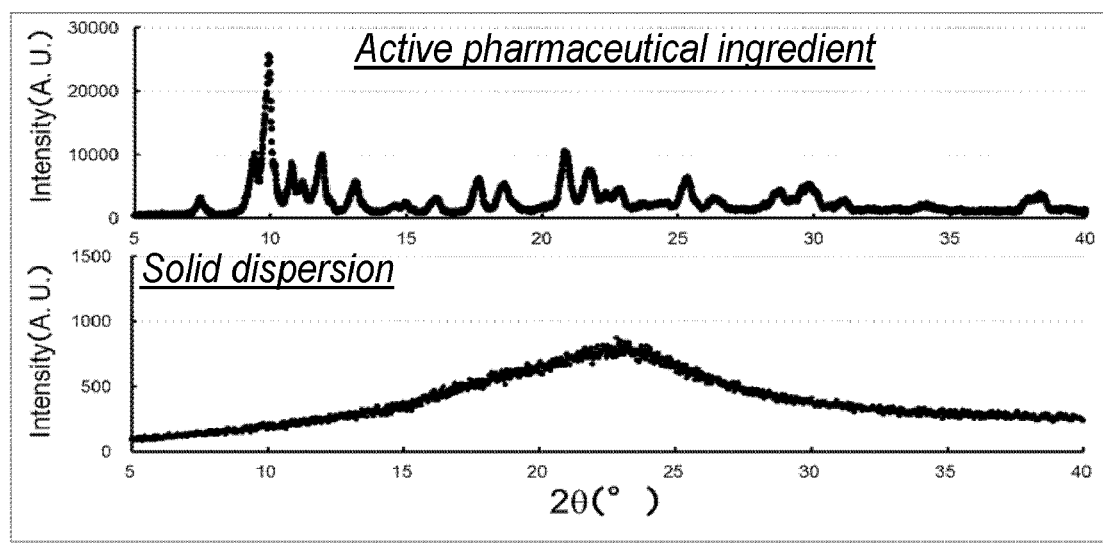
FIG. 21 shows powder X-ray diffraction results of nobiletin (upper figure) and nobiletin-αG hesperidin PA-T solid dispersion (lower figure) of Example 20.

A powder X-ray diffraction of the solid dispersion is shown in FIG. 21. As in Example 1, the amorphization of nobiletin in the solid dispersion was confirmed. The results of the above [Evaluation on time-course solubility] and [Caco-2 cell membrane permeability evaluation] are shown in Table 1-3.

Example 21

Five g of a powder (containing 14 mass % nobiletin) in which PMF90 (manufactured by Okinawa Research Center) and αG hesperidin PA-T (manufactured by Toyo Sugar Refining Co., Ltd.) were mixed respectively in a ratio of 25 mass % to 75 mass % was mixed with 50 mL of water containing 80 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 130° C., an outlet gas temperature: 78° C., a solution supply speed: 360 mL/h, a spray nitrogen flow rate: 414 L/h, and an aspirator flow rate: 35 m$^3$/h to prepare a solid dispersion. The obtained solid dispersion was 1.58 g (yield 32%).

Figure 22:
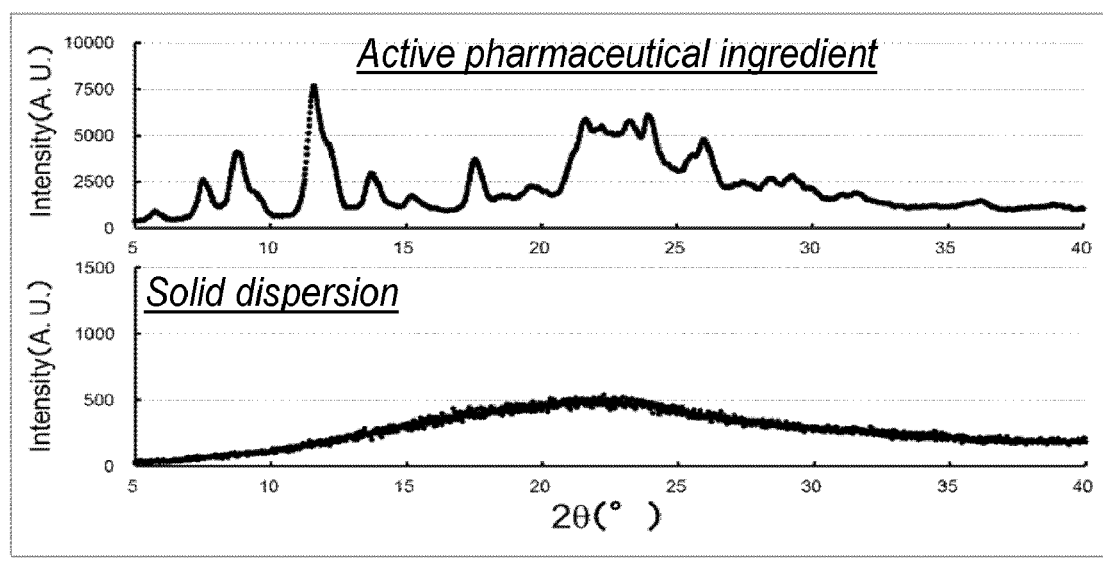
FIG. 22 shows powder X-ray diffraction results of PMF90 (upper figure) and PMF90-αG hesperidin PA-T solid dispersion (lower figure) of Example 21.

A powder X-ray diffraction of the solid dispersion is shown in FIG. 22. As in Example 1, the amorphization of nobiletin in the solid dispersion was confirmed. The results of the above [Evaluation on time-course solubility] and [Caco-2 cell membrane permeability evaluation] are shown in Table 1-3.

Example 22

Five g of a powder in which PMF90 (manufactured by Okinawa Research Center) and αG hesperidin PA-T (manufactured by Toyo Sugar Refining Co., Ltd.) were mixed respectively in a ratio of 40 mass % to 60 mass % was mixed with 50 mL of water containing 80 vol % ethanol. When the suspension was shaken at 60° C. for 5 minutes, a clear solution was obtained.

The solution was spray dried using spray dryer B-290 (manufactured by Nihon BUCHI K.K.) under the conditions of an inlet gas temperature: 110° C., an outlet gas temperature: 70° C., a solution supply speed: 360 mL/h, a spray nitrogen flow rate: 414 L/h, and an aspirator flow rate: 35 m$^3$/h to prepare a solid dispersion. The obtained solid dispersion was 1.03 g (yield 21%).

Figure 23:
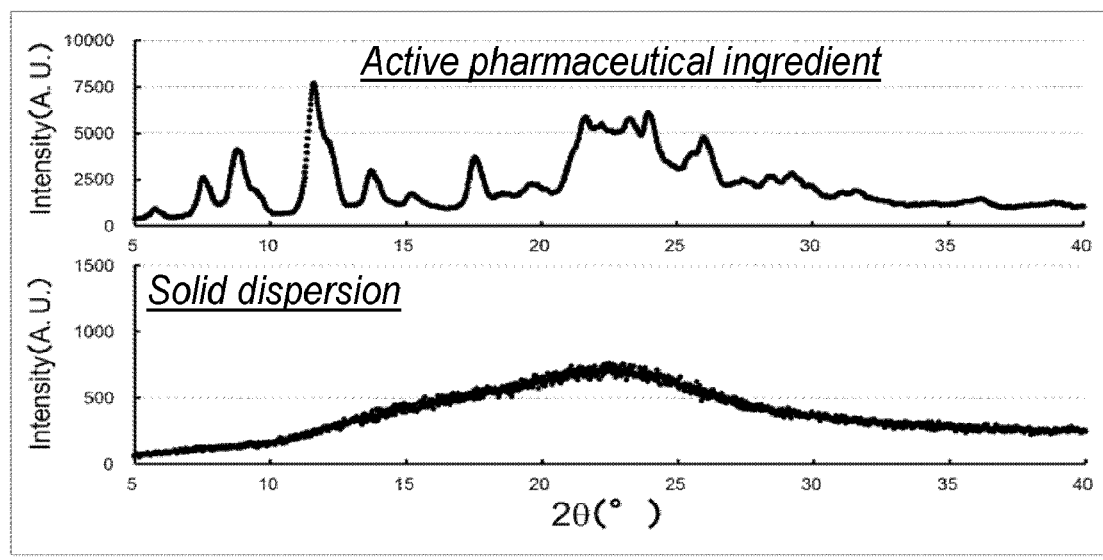
FIG. 23 shows powder X-ray diffraction results of PMF90 (upper figure) and PMF90-αG hesperidin PA-T solid dispersion (lower figure) of Example 22.

A powder X-ray diffraction of the solid dispersion is shown in FIG. 23. As in Example 1, the amorphization of nobiletin in the solid dispersion was confirmed. The results of the above [Evaluation on time-course solubility] and [Caco-2 cell membrane permeability evaluation] are shown in Table 1-3.

Comparative Example 1

Two point nine four g of a powder in which an ellagic acid dihydrate (manufactured by Tokyo Chemical Industry Co., Ltd.) and methyl hesperidin (manufactured by Tokyo Chemical Industry Co., Ltd.) were mixed respectively in a ratio of 18.4 mass % to 80.6 mass % was mixed with 150 mL of water containing 80 vol % ethanol. When the suspension was shaken at 60° C. for 5 minutes, a clear solution was not obtained but a suspension in which the powder was homogeneously dispersed was obtained.

The solution was spray dried using spray dryer B-290 (manufactured by Nihon BUCHI K.K.) under the conditions of an inlet gas temperature: 130° C., an outlet gas temperature: 75° C., a solution supply speed: 360 mL/h, a spray nitrogen flow rate: 414 L/h, and an aspirator flow rate: 35 m$^3$/h to prepare a solid dispersion. The obtained solid dispersion was 1.95 g (yield 66%).

Figure 24:
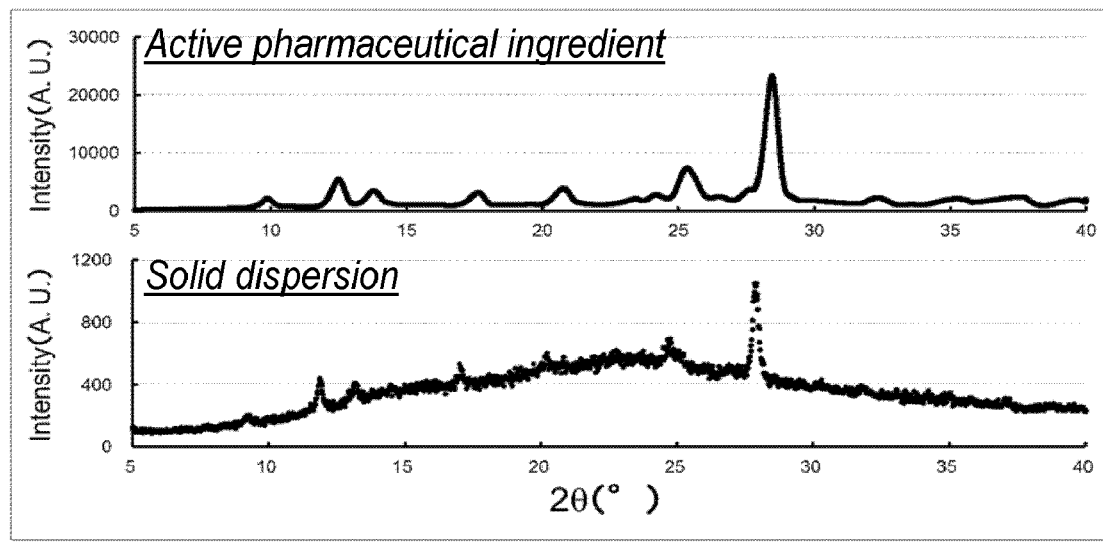
FIG. 24 shows powder X-ray diffraction results of ellagic acid (upper figure) and ellagic acid-methyl hesperidin solid dispersion (lower figure) of Comparative Example 1.

A powder X-ray diffraction of the solid dispersion is shown in FIG. 24. As in Example 1, the amorphization of ellagic acid in the solid dispersion was confirmed. The results of the above [Evaluation on time-course solubility] and [Caco-2 cell membrane permeability evaluation] are shown in Table 1-4.

Comparative Example 2

Two point nine four g of a powder in which an ellagic acid dihydrate (manufactured by Tokyo Chemical Industry Co., Ltd.) and methyl hesperidin (manufactured by Tokyo Chemical Industry Co., Ltd.) were mixed respectively in a ratio of 18.4 mass % to 80.6 mass % was mixed with 300 mL of water containing 80 vol % ethanol. When the suspension was shaken at 60° C. for 5 minutes, a clear solution was not obtained but a suspension in which the powder was homogeneously dispersed was obtained.

The solution was spray dried using spray dryer B-290 (manufactured by Nihon BUCHI K.K.) under the conditions of an inlet gas temperature: 130° C., an outlet gas temperature: 83° C., a solution supply speed: 360 mL/h, a spray nitrogen flow rate: 414 L/h, and an aspirator flow rate: 35 m³/h to prepare a solid dispersion. The obtained solid dispersion was 1.21 g (yield 41%).

Figure 25:
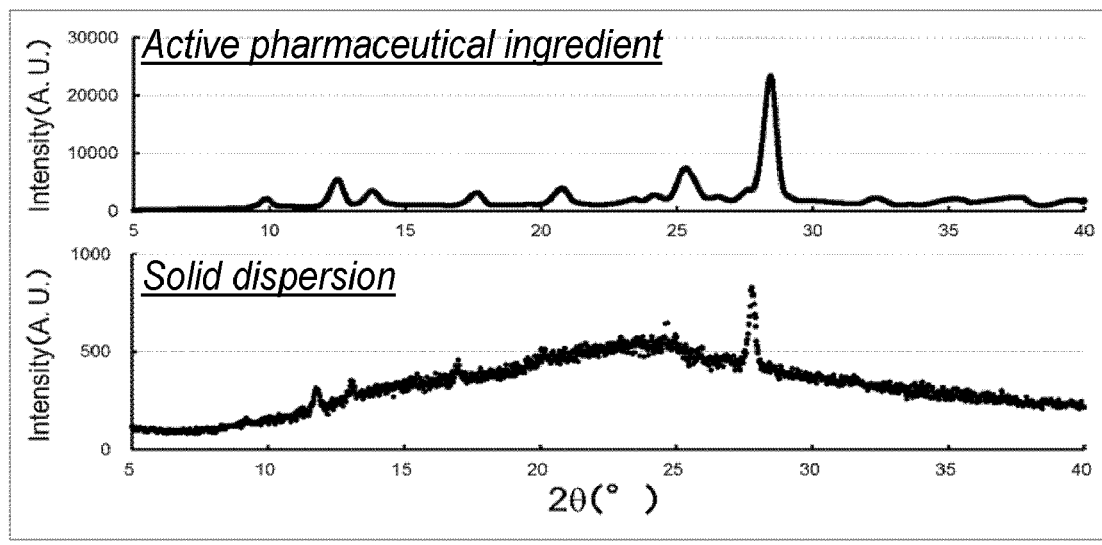
FIG. 25 shows powder X-ray diffraction results of ellagic acid (upper figure) and ellagic acid-methyl hesperidin solid dispersion (lower figure) of Comparative Example 2.

A powder X-ray diffraction of the solid dispersion is shown in FIG. 25. As in Example 1, the amorphization of ellagic acid in the solid dispersion was confirmed. The results of the above [Evaluation on time-course solubility] and [Caco-2 cell membrane permeability evaluation] are shown in Table 1-4.

Comparative Example 3

Two point nine four g of a powder in which an ellagic acid dihydrate (manufactured by Tokyo Chemical Industry Co., Ltd.) and methyl hesperidin (manufactured by Tokyo Chemical Industry Co., Ltd.) were mixed respectively in a ratio of 18.4 mass % to 80.6 mass % was mixed with 150 mL of water containing 95 vol % ethanol. When the suspension was shaken at 60° C. for 5 minutes, a clear solution was not obtained but a suspension in which the powder was homogeneously dispersed was obtained.

Figure 26:
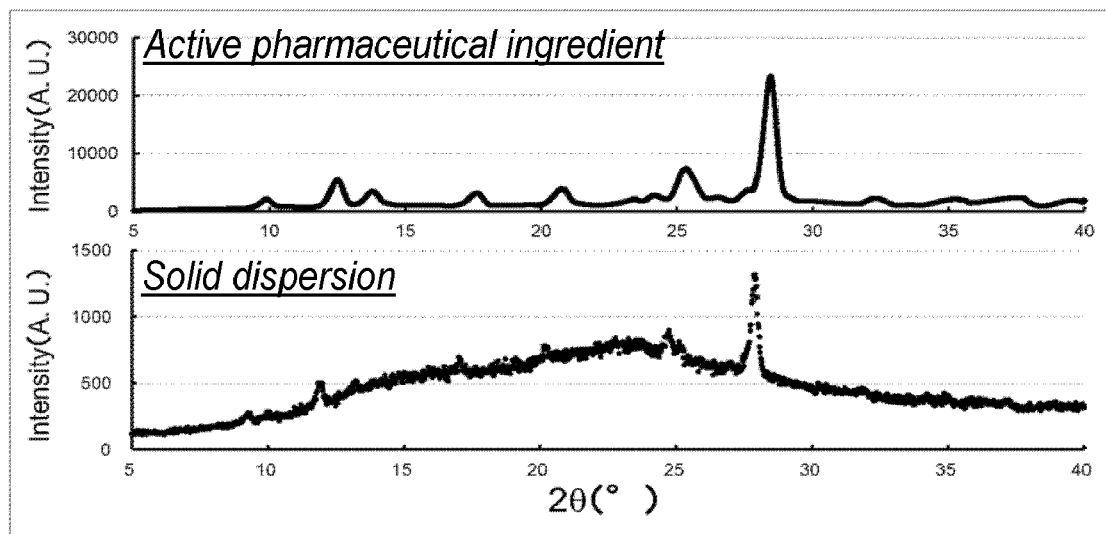
FIG. 26 shows powder X-ray diffraction results of ellagic acid (upper figure) and ellagic acid-methyl hesperidin solid dispersion (lower figure) of Comparative Example 3.

The solution was spray dried using spray dryer B-290 (manufactured by Nihon BUCHI K.K.) under the conditions of an inlet gas temperature: 130° C., an outlet gas temperature: 75° C., a solution supply speed: 360 mL/h, a spray nitrogen flow rate: 414 L/h, and an aspirator flow rate: 35 m³/h to prepare a solid dispersion. The obtained solid dispersion was 1.58 g (yield 54%). A powder X-ray diffraction of the solid dispersion is shown in FIG. 26. As in Example 1, the amorphization of ellagic acid in the solid dispersion was confirmed. The results of the above [Evaluation on time-course solubility] and [Caco-2 cell membrane permeability evaluation] are shown in Table 1-4.

Comparative Example 4

Two point nine four g of a powder in which an ellagic acid dihydrate (manufactured by Tokyo Chemical Industry Co., Ltd.) and methyl hesperidin (manufactured by Tokyo Chemical Industry Co., Ltd.) were mixed respectively in a ratio of 18.4 mass % to 80.6 mass % was mixed with 150 mL of water containing 50 vol % ethanol. When the suspension was shaken at 60° C. for 5 minutes, a clear solution was not obtained but a suspension in which the powder was homogeneously dispersed was obtained.

The solution was spray dried using spray dryer B-290 (manufactured by Nihon BUCHI K.K.) under the conditions of an inlet gas temperature: 130° C., an outlet gas temperature: 83° C., a solution supply speed: 360 mL/h, a spray nitrogen flow rate: 414 L/h, and an aspirator flow rate: 35 m³/h to prepare a solid dispersion. The obtained solid dispersion was 1.92 g (yield 65%).

Figure 27:
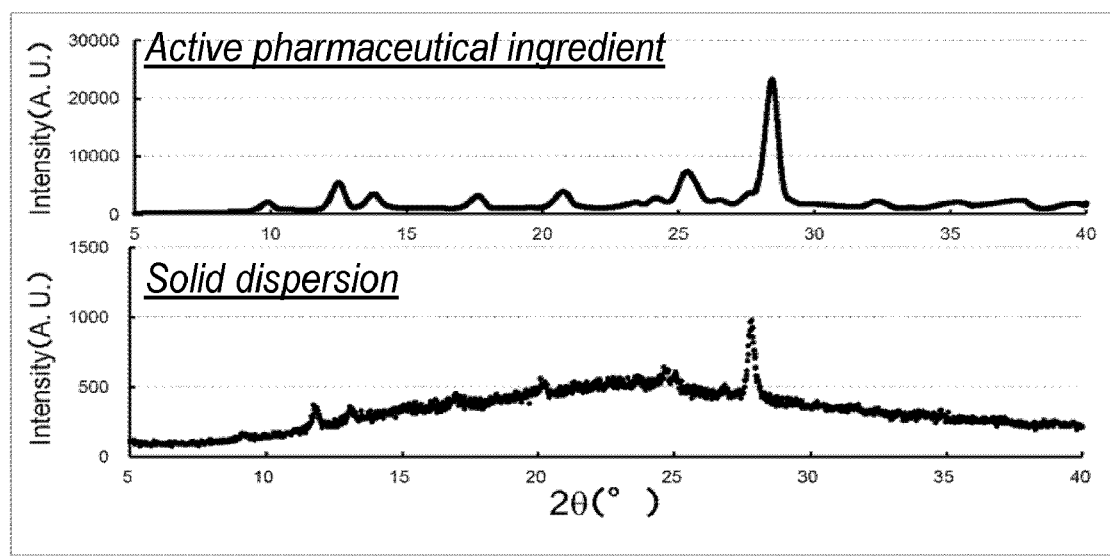
FIG. 27 shows powder X-ray diffraction results of ellagic acid (upper figure) and ellagic acid-methyl hesperidin solid dispersion (lower figure) of Comparative Example 4.

A powder X-ray diffraction of the solid dispersion is shown in FIG. 27. As in Example 1, the amorphization of ellagic acid in the solid dispersion was confirmed. The results of the above [Evaluation on time-course solubility] and [Caco-2 cell membrane permeability evaluation] are shown in Table 1-4.

Comparative Example 5

A mixture in which nobiletin (manufactured by Wako Pure Chemical Industries, Ltd.) as the poorly water-soluble substance and methyl hesperidin (manufactured by Tokyo Chemical Industry Co., Ltd.) were mixed respectively in a ratio of 25 mass % to 75 mass % was evaluated. The results of the above [Evaluation on time-course solubility] and [Caco-2 cell membrane permeability evaluation] are shown in Table 1-4.

Comparative Example 6

A mixture (containing 14 mass % nobiletin) in which PMF90 (manufactured by Okinawa Research Center) as the poorly water-soluble substance and methyl hesperidin (manufactured by Tokyo Chemical Industry Co., Ltd.) were mixed respectively in a ratio of 25 mass % to 75 mass % was evaluated. The results of the above [Evaluation on time-course solubility] and [Caco-2 cell membrane permeability evaluation] are shown in Table 1-4.

Comparative Example 7

A mixture (containing 14 mass % nobiletin) in which PMF90 (manufactured by Okinawa Research Center) as the poorly water-soluble substance and αG hesperidin PA-T (manufactured by Toyo Sugar Refining Co., Ltd.) were mixed respectively in a ratio of 25 mass % to 75 mass % was evaluated. The results of the above [Evaluation on time-course solubility] and [Caco-2 cell membrane permeability evaluation] are shown in Table 1-4.

TABLE 1-1

|  |  |  | Example 1 | Example 2 | Example 3 | Example 4 | Example 5 | Example 6 | Example 7 | Example 8 |
|---|---|---|---|---|---|---|---|---|---|---|
| Ingredient mixture | Poorly water-soluble substance |  | Nobiletin | Nobiletin | Nobiletin | Nobiletin | Nobiletin | Nobiletin | Nobiletin | Nobiletin |
|  | Solubility in 25° C. water | [ppm] | 1 | 1 | 1 | 1 | 1 | 1 | 1 | 1 |
|  | Auxiliary agent |  | MeHes | MeHes | MeHes | MeHes | MeHes | MeHes | MeHes | MeHes |
|  | Poorly water-soluble substance/auxiliary agent weight ratio |  | 0.33 | 0.33 | 0.33 | 0.33 | 0.33 | 0.33 | 0.33 | 0.33 |
|  | Nobiletin ratio | [Mass %] | 25% | 25% | 25% | 25% | 25% | 25% | 25% | 25% |
| Solution preparation conditions | Spray liquid poorly water-soluble substance concentration | [w/v %] | 2.5 | 1.25 | 2.5 | 2.5 | 2.5 | 2.5 | 2.5 | 2.5 |
|  | Spray liquid auxiliary agent concentration | [w/v %] | 7.5 | 3.75 | 7.5 | 7.5 | 7.5 | 7.5 | 7.5 | 7.5 |

TABLE 1-1-continued

|  |  |  | Example 1 | Example 2 | Example 3 | Example 4 | Example 5 | Example 6 | Example 7 | Example 8 |
|---|---|---|---|---|---|---|---|---|---|---|
|  | EtOH ratio in water-containing EtOH solvent | [%] | 50 | 50 | 80 | 50 | 95 | 20 | 50 | 50 |
|  | Heating temperature | [° C.] | 60 | 60 | 60 | 60 | 60 | 60 | 60 | 60 |
|  | Dissolution state after heated and left at room temperature for 10 min |  | Dissolved | Dissolved | Dissolved | Dissolved | Dissolved | Dissolved | Dissolved | Dissolved |
| Treatment conditions | Spray liquid spray volume | [mL] | 50 | 50 | 50 | 50 | 50 | 50 | 30 | 50 |
|  | Inlet gas temperature | [° C.] | 130 | 130 | 130 | 110 | 130 | 130 | 130 | 130 |
|  | Outlet gas temperature | [° C.] | 76 | 76 | 78 | 60 | 76 | 74 | 77 | 77 |
|  | Spray solution supply speed (mL/h) | [mL/h] | 360 | 360 | 360 | 360 | 360 | 360 | 180 | 360 |
|  | Spray nitrogen flow rate (m3/h) | [L/h] | 414 | 414 | 414 | 414 | 414 | 414 | 414 | 207 |
|  | Aspirator flow rate (m3/h) | [N · m] | 35 | 35 | 35 | 35 | 35 | 35 | 35 | 35 |
| Yield | Yield | [g] | 1.73 | 0.75 | 2.17 | 2.32 | 3.27 | 2.79 | 1.25 | 0.23 |
| Evaluation results | Poorly water-soluble substance time-course solubility (area under the curve) | [ppm · min] | 1.13E+05 | 1.12E+05 | 1.23E+05 | 1.06E+05 | 1.32E+05 | 1.56E+05 | 1.45E+05 | 1.41E+05 |
|  | Cell membrane permeability evaluation Poorly water-soluble substance concentration at starting insert upper portion evaluation | [μM] | 41.8 | 41.6 | 96.9 | 103.1 | 96.9 | 103.1 | 182.2 | 184.5 |
|  | Cell membrane permeability evaluation Poorly water-soluble substance concentration at completing insert lower portion evaluation | [μM] | 1.08 | 1.23 | 1.98 | 2.04 | 1.97 | 1.96 | 4.73 | 4.79 |
|  | Cell membrane permeability evaluation Poorly water-soluble substance concentration at completing insert lower portion evaluation standard error | [μM] | 0.08 | 0.04 | 0.15 | 0.14 | 0.13 | 0.16 | 0.31 | 0.63 |
|  | Cell viability evaluation by LDH Assay | [%] | 94.0 | 94.1 | 94.2 | 94 | 94.1 | 94.2 | 94.3 | 92.9 |
|  | Cell viability evaluation by LDH Assay standard error | [%] | 0.2 | 0.1 | 0.6 | 0.1 | 0.1 | 0.4 | 0.0 | 1.5 |

TABLE 1-2

| | | | Example 9 | Example 10 | Example 11 | Example 12 | Example 13 | Example 14 | Example 15 | Example 16 |
|---|---|---|---|---|---|---|---|---|---|---|
| Ingredient mixture | Poorly water-soluble substance | | Nobiletin | Nobiletin | Nobiletin | Nobiletin | Nobiletin | PMF90 | PMF90 | PMF90 |
| | Solubility in 25° C. water | [ppm] | 1 | 1 | 1 | 1 | 1 | 1 | 1 | 1 |
| | Auxiliary agent | | MeHes | MeHes | MeHes | MeHes | MeHes | MeHes | MeHes | MeHes |
| | Poorly water-soluble substance/ auxiliary agent weight ratio | | 0.33 | 0.33 | 0.05 | 1.00 | 0.67 | 0.05 | 1.00 | 0.67 |
| | Nobiletin ratio | [Mass %] | 25% | 25% | 5% | 50% | 40% | 5% | 50% | 40% |
| Solution preparation conditions | Spray liquid poorly water-soluble substance concentration | [w/v %] | 2.5 | 2.5 | 1.0 | 5.0 | 4.0 | 2.5 | 5.0 | 4.0 |
| | Spray liquid auxiliary agent concentration | [w/v %] | 7.5 | 7.5 | 9.0 | 5.0 | 6.0 | 7.5 | 5.0 | 6.0 |
| | EtOH ratio in water-containing EtOH solvent | [%] | 50 | 50 | 50 | 50 | 50 | 50 | 50 | 50 |
| | Heating temperature | [° C.] | 60 | 60 | 60 | 60 | 60 | 60 | 60 | 60 |
| | Dissolution state after heated and left at room temperature for 10 min | | Dissolved | Dissolved | Dissolved | Dissolved | Dissolved | Dissolved | Dissolved | Dissolved |
| Treatment conditions | Spray liquid spray volume | [mL] | 50 | 50 | 50 | 50 | 50 | 50 | 50 | 50 |
| | Inlet gas temperature | [° C.] | 130 | 130 | 130 | 130 | 130 | 130 | 130 | 130 |
| | Outlet gas temperature | [° C.] | 73 | 70 | 71 | 72 | 76 | 78 | 78 | 77 |
| | Spray solution supply speed (mL/h) | [mL/h] | 540 | 360 | 360 | 360 | 360 | 360 | 360 | 360 |
| | Spray nitrogen flow rate (m3/h) | [L/h] | 414 | 621 | 414 | 414 | 414 | 414 | 414 | 414 |
| | Aspirator flow rate (m3/h) | [N · m] | 35 | 35 | 35 | 35 | 35 | 35 | 35 | 35 |
| Yield | Yield | [g] | 1.26 | 0.62 | 2.46 | 0.59 | 1.95 | 1.18 | 0.13 | 1.7 |
| Evaluation results | Poorly water-soluble substance time-course solubility (area under the curve) | [ppm · min] | 1.67E+05 | 1.52E+05 | 1.13E+05 | 4.42E+04 | 6.50E+04 | 1.92E+05 | 4.24E+04 | 1.15E+05 |
| | Cell membrane permeability evaluation Poorly water-soluble substance concentration at starting insert upper portion evaluation | [μM] | 149.2 | 146.8 | 79.7 | 119.2 | 88.0 | 88.3 | 92.8 | 109.6 |
| | Cell membrane permeability evaluation Poorly water-soluble substance concentration at completing insert lower portion evaluation | [μM] | 2.31 | 2.18 | 0.84 | 1.38 | 1.28 | 1.27 | 1.50 | 1.93 |

TABLE 1-2-continued

|  |  | Example 9 | Example 10 | Example 11 | Example 12 | Example 13 | Example 14 | Example 15 | Example 16 |
|---|---|---|---|---|---|---|---|---|---|
| Cell membrane permeability evaluation Poorly water-soluble substance concentration at completing insert lower portion evaluation standard error | [μM] | 0.27 | 0.29 | 0.11 | 0.24 | 0.34 | 0.22 | 0.09 | 0.59 |
| Cell viability evaluation by LDH Assay | [%] | 92.9 | 93.6 | 93.8 | 94.0 | 94.1 | 94.6 | 94.2 | 94.0 |
| Cell viability evaluation by LDH Assay standard error | [%] | 1.7 | 2.4 | 1.0 | 0.8 | 0.5 | 0.3 | 0.3 | 0.3 |

TABLE 1-3

|  |  |  | Example 17 | Example 18 | Example 19 | Example 20 | Example 21 | Example 22 |
|---|---|---|---|---|---|---|---|---|
| Ingredient mixture | Poorly water-soluble substance |  | Nobiletin | Nobiletin | Nobiletin | Nobiletin | PMF90 | PMF90 |
|  | Solubility in 25° C. water | [ppm] | 1 | 1 | 1 | 1 | 1 | 1 |
|  | Auxiliary agent |  | aGHes PA-T | aGHes PA-T | aGHes PA-T | aGHes PA-T | aGHes PA-T | aGHes PA-T |
|  | Poorly water-soluble substance/auxiliary agent weight ratio |  | 0.33 | 0.33 | 0.67 | 0.33 | 0.33 | 0.67 |
|  | Nobiletin ratio | [Mass %] | 25% | 25% | 40% | 25% | 25% | 40% |
| Solution preparation conditions | Spray liquid poorly water-soluble substance concentration | [w/v %] | 2.5 | 2.5 | 4.0 | 2.5 | 2.5 | 4.0 |
|  | Spray liquid auxiliary agent concentration | [w/v %] | 7.5 | 7.5 | 6.0 | 7.5 | 7.5 | 6.0 |
|  | EtOH ratio in water-containing EtOH solvent | [%] | 80 | 80 | 80 | 50 | 80 | 80 |
|  | Heating temperature | [° C.] | 60 | 60 | 60 | 60 | 60 | 60 |
|  | Dissolution state after heated and left at room temperature for 10 min |  | Dissolved | Dissolved | Dissolved | Dissolved | Dissolved | Dissolved |
| Treatment conditions | Spray liquid spray volume | [mL] | 50 | 50 | 50 | 50 | 50 | 50 |
|  | Inlet gas temperature | [° C.] | 130 | 110 | 130 | 130 | 130 | 110 |
|  | Outlet gas temperature | [° C.] | 74 | 66 | 78 | 83 | 80 | 70 |
|  | Spray solution supply speed (mL/h) | [mL/h] | 360 | 360 | 360 | 360 | 360 | 360 |
|  | Spray nitrogen flow rate (m3/h) | [L/h] | 414 | 414 | 414 | 414 | 414 | 414 |
|  | Aspirator flow rate (m3/h) | [N · m] | 35 | 35 | 35 | 35 | 35 | 35 |
| Yield | Yield | [g] | 1.33 | 1.81 | 1.33 | 1.46 | 1.58 | 1.46 |
| Evaluation results | Poorly water-soluble substance time-course solubility (area under the curve) | [ppm · min] | 3.15E+04 | 3.10E+04 | 1.66E+04 | 2.61E+04 | 7.53E+04 | 6.36E+04 |
|  | Cell membrane permeability evaluation Poorly water-soluble substance concentration at starting insert upper portion evaluation | [μM] | 94.5 | 112.6 | 51.0 | 52.2 | 86.3 | 61.7 |
|  | Cell membrane permeability evaluation Poorly water-soluble substance concentration at completing insert lower portion evaluation | [μM] | 1.55 | 2.05 | 0.33 | 1.29 | 1.54 | 2.24 |

TABLE 1-3-continued

|  |  | Example 17 | Example 18 | Example 19 | Example 20 | Example 21 | Example 22 |
|---|---|---|---|---|---|---|---|
| Cell membrane permeability evaluation Poorly water-soluble substance concentration at completing insert lower portion evaluation standard error | [μM] | 0.11 | 0.25 | 0.06 | 0.58 | 0.06 | 0.08 |
| Cell viability evaluation by LDH Assay | [%] | 94.5 | 94.7 | 94.5 | 94.0 | 94.3 | 83.3 |
| Cell viability evaluation by LDH Assay standard error | [%] | 0.9 | 0.2 | 0.8 | 1.1 | 1.0 | 21.8 |

TABLE 1-4

|  |  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Ingredient mixture | Poorly water-soluble substance |  | Ellagic acid | Ellagic acid | Ellagic acid | Ellagic acid | Nobiletin | PMF90 | PMF90 |
|  | Solubility in 25° C. water | [ppm] | 4 | 4 | 4 | 4 | 1 | 1 | 1 |
|  | Auxiliary agent |  | MeHes | MeHes | MeHes | MeHes | MeHes | MeHes | aGHes PA-T |
|  | Poorly water-soluble substance/auxiliary agent weight ratio |  | 0.23 | 0.23 | 0.23 | 0.23 | 0.33 | 0.33 | 0.33 |
|  | Nobiletin ratio | [Mass %] | — | — | — | — | 25% | 15% | 15% |
| Solution preparation conditions | Spray liquid poorly water-soluble substance concentration | [w/v %] | 0.36 | 0.18 | 0.36 | 0.36 | No dissolution or spray dry treatment | No dissolution or spray dry treatment | No dissolution or spray dry treatment |
|  | Spray liquid auxiliary agent concentration | [w/v %] | 1.6 | 0.8 | 1.6 | 1.6 |  |  |  |
|  | EtOH ratio in water-containing EtOH solvent | [%] | 80 | 80 | 95 | 50 |  |  |  |
|  | Heating temperature | [° C.] | 60 | 60 | 60 | 60 |  |  |  |
|  | Dissolution state after heated and left at room temperature for 10 min |  | Suspended | Suspended | Suspended | Suspended |  |  |  |
| Treatment conditions | Spray liquid spray volume | [mL] | 150 | 300 | 150 | 150 |  |  |  |
|  | Inlet gas temperature | [° C.] | 130 | 130 | 130 | 130 |  |  |  |
|  | Outlet gas temperature | [° C.] | 75 | 83 | 84 | 83 |  |  |  |
|  | Spray solution supply speed (mL/h) | [mL/h] | 360 | 360 | 360 | 360 |  |  |  |
|  | Spray nitrogen flow rate (m3/h) | [L/h] | 414 | 414 | 414 | 414 |  |  |  |
|  | Aspirator flow rate (m3/h) | [N · m] | 35 | 35 | 35 | 35 |  |  |  |
| Yield Evaluation results | Yield | [g] | 1.95 | 1.21 | 1.58 | 1.92 |  |  |  |
|  | Poorly water-soluble substance time-course solubility (area under the curve) | [ppm · min] | 4.73E+03 | 5.16E+03 | 4.73E+03 | 4.01E+03 | 1.76E+04 | 1.44E+04 | 3.76E+04 |
|  | Cell membrane permeability evaluation Poorly water-soluble substance concentration at starting insert upper portion evaluation | [μM] | 2.42 | 1.69 | 1.00 | 1.81 | 17.53 | 51 | 29.5 |

TABLE 1-4-continued

|  |  | Comparative Example 1 | Comparative Example 2 | Comparative Example 3 | Comparative Example 4 | Comparative Example 5 | Comparative Example 6 | Comparative Example 7 |
| --- | --- | --- | --- | --- | --- | --- | --- | --- |
| Cell membrane permeability evaluation Poorly water-soluble substance concentration at completing insert lower portion evaluation | [µM] | 0.0080 | 0.0089 | 0.0045 | 0.0085 | 0.242 | 1.91 | 0.76 |
| Cell membrane permeability evaluation Poorly water-soluble substance concentration at completing insert lower portion evaluation standard error | [µM] | 0.0012 | 0.0028 | 0.0079 | 0.0010 | 0.027 | 0.05 | 0.085 |
| Cell viability evaluation by LDH Assay | [%] | 94.3 | 94 | 94.6 | 94.3 | 94.4 | 94.5 | 95.2 |
| Cell viability evaluation by LDH Assay standard error | [%] | 0.4 | 0.2 | 0.6 | 0.2 | 0.013 | 1.54 | 1.25 |

The invention claimed is:

1. A method for producing a solid dispersion comprising nobiletin, the method comprising:
dissolving nobiletin or a nobiletin-comprising substance and a water-soluble methyl hesperidin in an ethanol aqueous solution having an ethanol concentration of from 20 to 90 vol %; and
spray-drying the solution,
wherein a mass ratio of nobiletin to the water-soluble methyl hesperidin [nobiletin/water-soluble methyl hesperidin], when nobiletin or the nobiletin-comprising substance and the water-soluble methyl hesperidin are mixed, is from 0.01 to 0.67.

2. The method for producing a solid dispersion according to claim 1, wherein nobiletin or the nobiletin-comprising substance and the water-soluble methyl hesperidin are dissolved in the ethanol aqueous solution at from 0 to 90° C.

3. The method for producing a solid dispersion according to claim 1, wherein an ethanol concentration of the ethanol aqueous solution is from 30 to 88 vol %.

* * * * *